(12) United States Patent
Torres

(10) Patent No.: US 10,213,503 B2
(45) Date of Patent: Feb. 26, 2019

(54) **ATTENUATED *BURKHOLDERIA MALLEI* STRAIN WHICH PROTECTS AGAINST PATHOGENIC *BURKHOLDERIA* INFECTIONS, VACCINE CONTAINING AND USE THEREOF**

(71) Applicant: THE BOARD OF REGENTS OF THE UNIVERSITY OF TEXAS SYSTEM, Austin, TX (US)

(72) Inventor: Alfredo G. Torres, Friendswood, TX (US)

(73) Assignee: THE BOARD OF TRUSTEES OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/598,787

(22) Filed: May 18, 2017

(65) Prior Publication Data

US 2017/0333543 A1 Nov. 23, 2017

Related U.S. Application Data

(60) Provisional application No. 62/338,630, filed on May 19, 2016.

(51) Int. Cl.

| | | |
|---|---|---|
| *A61K 39/02* | (2006.01) | |
| *A61K 9/12* | (2006.01) | |
| *C12N 1/36* | (2006.01) | |
| *C07K 14/195* | (2006.01) | |
| *A61K 39/00* | (2006.01) | |
| *C12N 15/74* | (2006.01) | |
| *A61K 39/104* | (2006.01) | |
| *A61K 9/00* | (2006.01) | |

(52) U.S. Cl.
CPC .......... *A61K 39/0208* (2013.01); *A61K 9/12* (2013.01); *A61K 39/104* (2013.01); *C07K 14/195* (2013.01); *C12N 1/36* (2013.01); *C12N 15/74* (2013.01); *A61K 9/0019* (2013.01); *A61K 9/0043* (2013.01); *A61K 9/0073* (2013.01); *A61K 2039/522* (2013.01); *A61K 2039/545* (2013.01); *A61K 2039/552* (2013.01); *A61K 2039/575* (2013.01)

(58) Field of Classification Search
CPC ........ A61K 2039/522; A61K 2039/545; A61K 2039/552; A61K 2039/575; A61K 39/0208; A61K 9/12; A61K 39/104; A61K 9/0019; A61K 9/0043; A61K 9/0073; C12N 15/74; C12N 1/36; C07K 14/195

See application file for complete search history.

(56) References Cited

U.S. PATENT DOCUMENTS

| | | |
|---|---|---|
| 5,705,188 A | 1/1998 | Junichi et al. |
| 9,267,947 B2 | 2/2016 | Torres et al. |

FOREIGN PATENT DOCUMENTS

WO 97/30731 8/1997

OTHER PUBLICATIONS

Wikipedia article on *Burkholderia*, pp. 1-4, Jan. 19, 2018.*
Schell et al. Mol. Microbiol. 64: 1466-1485, 2007.*
Kvitko et al. PLoS 6: e1715: 1-13, 2012.*
Amemiya K, et al. "Interleukin-12 induces a Th1-like response to Burkholderia mallei and limited protection in BALB/c mice," Vaccine. Feb. 27, 2006;24(9):1413-20.
Amemiya K, et al. "Nonviable Burkholderia mallei induces a mixed Th1-and Th2-like cytokine response in BALB/c mice," Infect Immun. May 2007;70(5):2319-25.
Bandara AB, et al. "A disruption of ctpA encoding carboxy-terminal protease attenuates Burkholderia mallei and induces partial protection in CD1 mice," Microb Pathog. Sep. 2008;45(3):207-16.
Bondi SK, et al. "Strategies toward vaccines against Burkholderia mallei and Burkholderia pseudomallei ," Expert Rev Vaccines. Nov. 2008;7(9):1357-65.
Brett PJ, et al. "Structural and immunological characterization of Burkholderia pseudomallei O-polysaccharide-flagellin protein conjugates," Infect Immun. Jul. 1996;64(7):2824-8.
Brett PJ, et al. "Isolation and characterization of Pseudomonas pseudomallei flagellin proteins," Infect Immun. May 1994;62(5):1914-9.
Bryan LE, et al. "Passive protection of diabetic rats with antisera specific for the polysaccharide portion of the lipopolysaccharide isolated from Pseudomonas pseudomallei," Can J Infect Dis. Jul. 1994;5(4):170-8.
Burtnick MN, et al. "The cluster 1 type VI secretion system is a major virulence determinant in Burkholderia pseudomallei," Infect Immun. Apr. 2011;79(4):1512-25.
Burtnick MN, et al. "Burkholderia mallei cluster 1 type VI secretion mutants exhibit growth and actin polymerization defects in RAW 264.7 murine macrophages," Infect Immun. Jan. 2010;78(1):88-99.
Choh LC, et al. "Burkholderia vaccines: are we moving forward?" Front Cell Infect Microbiol. Feb. 5, 2013;3:5.
Dance DA. "Melioidosis: the tip of the iceberg?" Clin Microbiol Rev. Jan. 1991;4(1):52-60.

(Continued)

*Primary Examiner* — Sarvamangala Devi
(74) *Attorney, Agent, or Firm* — Robin L. Teskin; LeClairRyan PLLC

(57) ABSTRACT

Herein we describe construction of a select agent-excluded *B. mallei* ΔtonB Δhcp1 (CLH001) vaccine strain and demonstrate its ability to protect against acute respiratory glanders. Particularly, CLH001 is shown to be attenuated, safe, and effective at protecting against lethal *B. mallei* challenge. This strain should be useful in vaccines are for use in humans and animals, e.g., equines, in treating or providing immunoprotection against infections elicited by category B, tier 1 pathogens, in particular *Burkholderia mallei* (Bm) and *B. pseudomallei*, the causative agents of human glanders and melioidosis, respectively.

14 Claims, 28 Drawing Sheets

Specification includes a Sequence Listing.

(56) References Cited

OTHER PUBLICATIONS

Duval CW, et al. "The Histological Lesions of Experimental Glanders," J Exp Med. Jul. 17, 1907;9 (4):352-80.
Galyov EE, et al. "Molecular insights into Burkholderia pseudomallei and Burkholderia mallei pathogenesis," Annu Rev Microbiol. 2010;64:495-517.
Horn JK. "Bacterial agents used for bioterrorism," Surg Infect (Larchmt). 2003 Fall;4(3):281-7.
Hornstra H, et al. "Molecular epidemiology of glanders, Pakistan," Emerg Infect Dis. Dec. 2009;15(12):2036-9.
Howe C, et al. "Human glanders; report of six cases," Ann Intern Med. Jan. 1947;26(1):93-115.
Judy BM, et al. "Prophylactic application of CpG oligonucleotides augments the early host response and confers protection in acute melioidosis," PLoS One. 2012;7(3):e34176.
Kespichayawattana W, et al. "Burkholderia pseudomallei induces cell fusion and actin-associated membrane protrusion: a possible mechanism for cell-to-cell spreading," Infect Immun. Sep. 2000;68(9):5377-84.
Khan et al. "Glanders in animals: a review on epidemiology, clinical presentation, diagnosis and countermeasures." Transboundary and emerging diseases. Jun. 2013;60(3):204-21.
Malik et al. "Emergence and re-emergence of glanders in India: a description of outbreaks from 2006 to 2011." Vet Ital. Apr. 1, 2012;48(2):167-78.
Massey et al. "In vivo bioluminescence imaging of Burkholderia mallei respiratory infection and treatment in the mouse model." Frontiers in microbiology. Aug. 26, 2011;2:174.
Mott et al. "Characterization of the Burkholderia mallei tonB mutant and its potential as a backbone strain for vaccine development." PLoS neglected tropical diseases. Jun. 26, 2015;9(6):e0003863.
Mougous et al. "A virulence locus of Pseudomonas aeruginosa encodes a protein secretion apparatus." Science. Jun. 9, 2006;312(5779):1526-30.
Nelson et al. "Evaluation of lipopolysaccharide and capsular polysaccharide as subunit vaccines against experimental melioidosis." Journal of medical microbiology. Dec. 1, 2004;53(12):1177-82.
Neubauer et al. "Serodiagnosis of Burkholderia mallei Infections in Horses: State-of-the-art and Perspectives." Journal of Veterinary Medicine, Series B. Jun. 2005;52(5):201-5.
Nieves et al. "A naturally derived outer-membrane vesicle vaccine protects against lethal pulmonary Burkholderia pseudomallei infection." Vaccine 29, 8381-8389 (2011).
Pukatzki et al. "Identification of a conserved bacterial protein secretion system in Vibrio cholerae using the Dictyostelium host model system." Proceedings of the National Academy of Sciences. Jan. 31, 2006;103(5):1528-33.
Sarkar-Tyson et al. "Progress toward development of vaccines against melioidosis: a review." Clinical therapeutics. Aug. 1, 2010;32(8):1437-45.
Schell et al. "Type VI secretion is a major virulence determinant in Burkholderia mallei." Molecular microbiology. Jun. 2007;64(6):1466-85.
Scholz et al. "Genotyping of Burkholderia mallei from an outbreak of glanders in Bahrain suggests multiple introduction events." PLoS neglected tropical diseases. Sep. 25, 2014;8(9):e3195.
Silva et al. "Development of Burkholderia mallei and pseudomallei vaccines." Frontiers in cellular and infection microbiology. Mar. 11, 2013;3:10.
Silva et al. "Correlates of immune protection following cutaneous immunization with an attenuated Burkholderia pseudomallei vaccine." Infection and immunity. Oct. 7, 2013:IAI-00915.
Srinivasan et al. "Glanders in a military research microbiologist." New England Journal of Medicine. Jul. 26, 2001;345(4):256-8.
Stone R. "Racing to defuse a bacterial time bomb." Science. Aug. 24, 2007;317(5841):1022-4.
Turner et al. "Construction and characterization of genetically definedaro omp mutants of Enterotoxigenic *Escherichia coli* and preliminary studies of safety and immunogenicity in humans." Infection and immunity. Aug. 1, 2001;69(8):4969-79.
Ulrich et al. "Aerogenic vaccination with a Burkholderia mallei auxotroph protects against aerosol-initiated glanders in mice." Vaccine. Mar. 14, 2005;23(16):1986-92.
Van Zandt KE. Glanders: an overview of infection in humans. Orphanet journal of rare diseases. Dec. 2013;8(1):131.
Verma, A.K. et al. Glanders—A re-emerging zoonotic disease: A review. Journal of Biological Sciences 14.1 (2014): 38-51.
Vollmer J, et al. "Characterization of three CpG oligodeoxynucleotide classes with distinct immunostimulatory activities," Eur J Immunol. Jan. 2004;34(1):251-62.
Wheelis M. "First shots fired in biological warfare," Nature. Sep. 17, 1998;395(6699):213.
Whitlock GC, et al. "Glanders: off to the races with Burkholderia mallei," FEMS Microbiol Lett. Dec. 2007;277(2):115-22.
Whitlock GC, et al. "Construction of a reporter system to study Burkholderia mallei type III secretion and identification of the BopA effector protein function in intracellular survival," Trans R Soc Trop Med Hyg. Dec. 2008;102 Suppl 1: S127-33.
Whitlock GC, et al. "Protective response to subunit vaccination against intranasal Burkholderia mallei and B. pseudomallei challenge," Procedia Vaccinol. 2010;2(1).

* cited by examiner

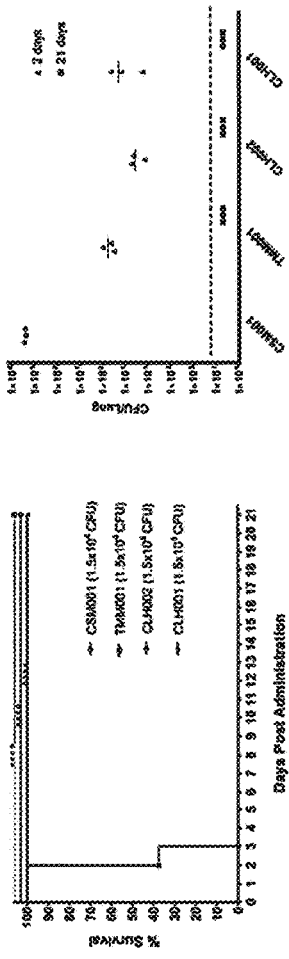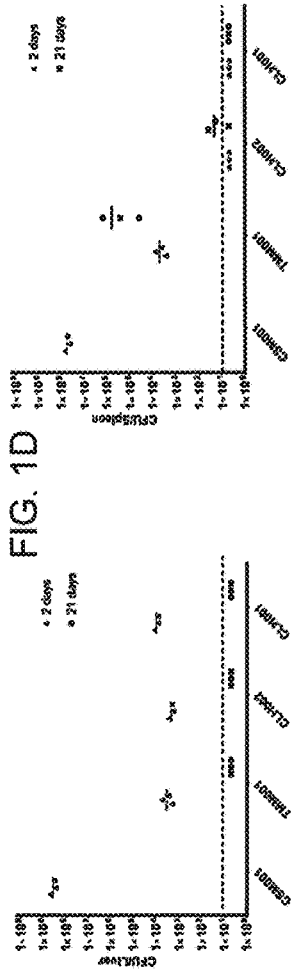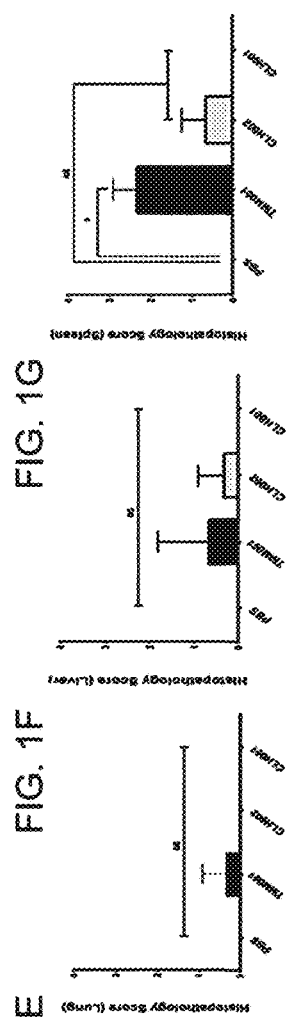
Figures 1A-G. CLH001 is highly attenuated in BALB/c mice compared to CSM001 strain and exhibits increased safety over TMM001 and CLH002 strains at day 21 post infection.

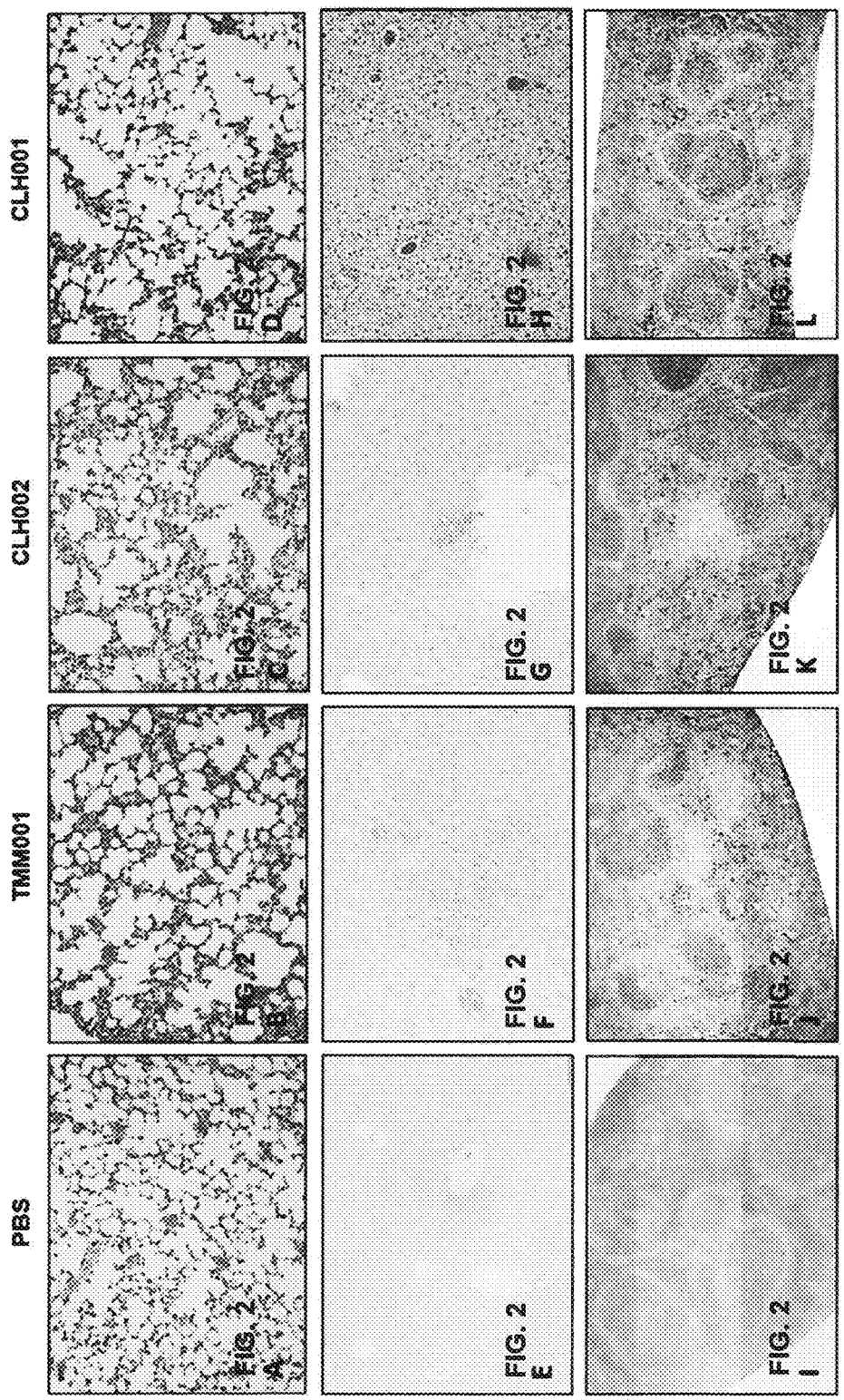
Figures 2.A-L. Representative images of organ pathology from challenged mice.

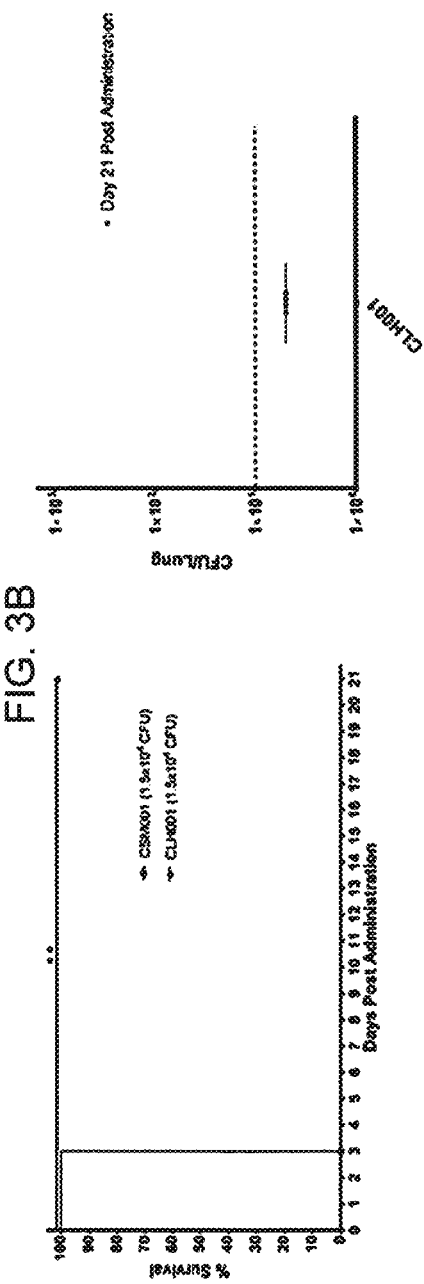
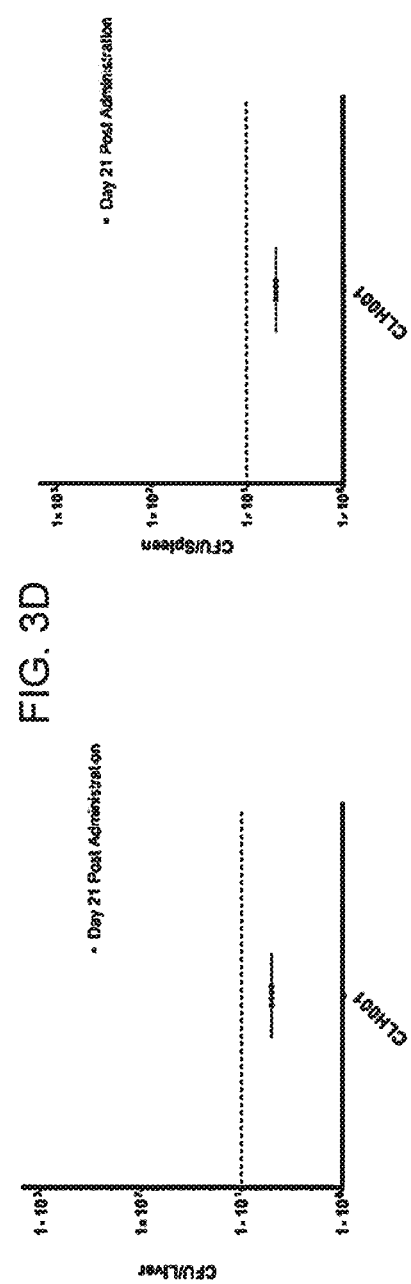
Figures 3A–D. NSG mice infected with CLH001 showed 100% survival and complete bacterial clearance.

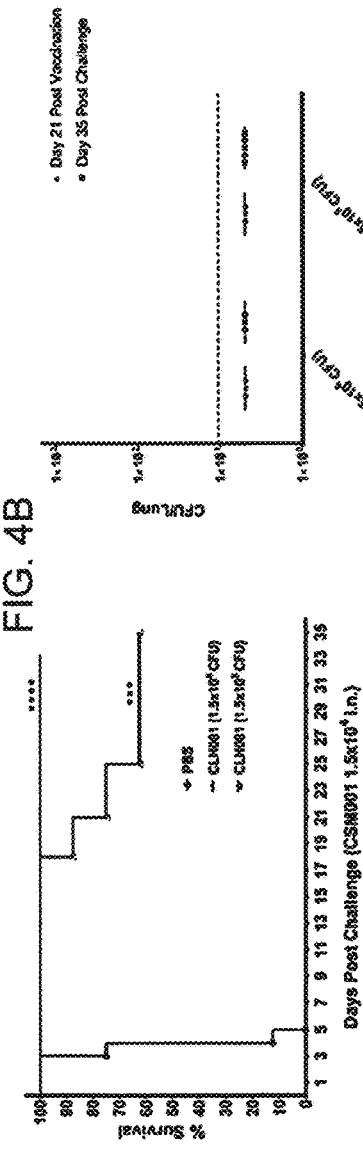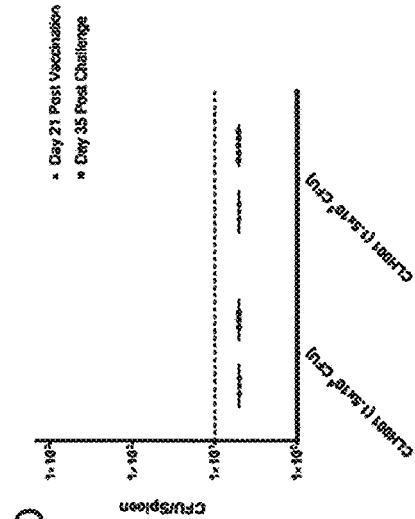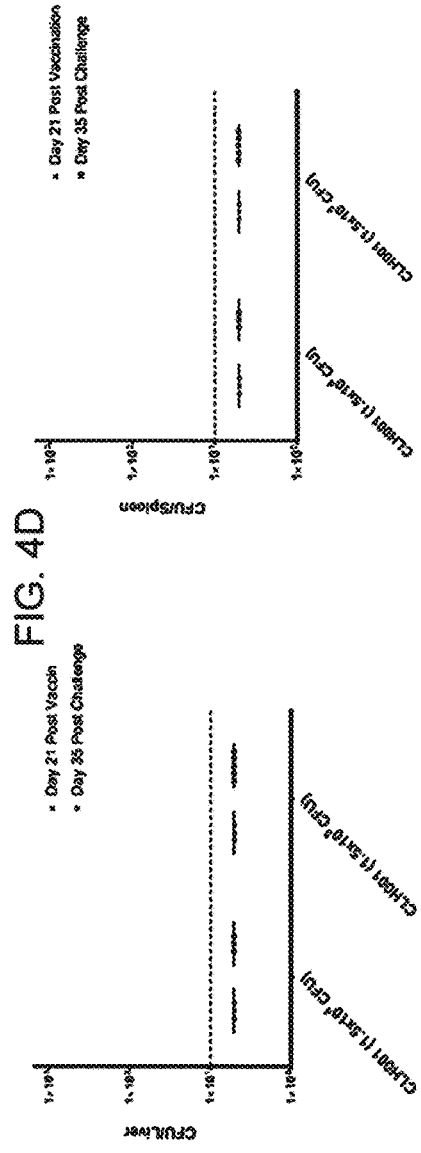
Figures 4A-D. Prime and boost vaccination with CLH001 ($1.5 \times 10^5$ CFU) provides 100% protection with no discernable organ colonization following CSM001 challenge.

Figures 5A-D. Vaccination with CLH001 (1.5×10⁵ CFU) provides significant protection following *B. mallei* 23344 high dose challenge, but bacterial organ colonization was observed.

Figure 6. CLH001 serum promotes killing of *B. mallei* 23344 *in vitro*.

B. mallei ΔtonB Attenuated Virulence is Partially Rescued by Iron Supplementation

Legend:
- ● 1.5x10$^5$ CFU
- ■ 1.5x10$^6$ CFU
- ▲ 1.5x10$^7$ CFU
- ○ 1.5x10$^5$ CFU + FeSO$_4$
- □ 1.5x10$^6$ CFU + FeSO$_4$
- △ 1.5x10$^7$ CFU + FeSO$_4$

FIG. 9

Gross Pathology of *B. mallei ΔtonB* and PBS Vaccinated Mice 21 Days Post Vaccination

FIG. 11

**Attenuated *B. mallei* Δ*tonB* Protects Against WT *B. mallei* Challenge**

**Histopathology of *B. mallei* Δ*tonB* Vaccinated vs. PBS Control Mice 48 h Post Challenge**

FIG. 14

**Cytokine Profiles of *B. mallei* Δ*tonB* Vaccinated vs. PBS Control Mice 48 h Post Challenge**

FIG. 15

The Pros and Cons of Using *B. mallei* Δ*tonB* as a Live Attenuated Vaccine

| Pros | Cons |
|---|---|
| 100% and 80% protection in acute inhalational models of murine glanders and melioidosis, respectively | Persistence |
| Wild type clearance | Reversion to wild type |
| Increases protective antibodies responses | Not usable for the immunocompromised |
| Localized infection/histopathology | |
| Reduces inflammation | |
| Enhances protective cytokine/chemokine responses | |

FIG. 17

FIG. 18 hcp1 and tonB Survival and Persistence Study

| Infection Strain | Dose (CFU/50μl) |
|---|---|
| B. mallei lux (WT) | $1.5 \times 10^4$ |
| B. mallei ΔtonB | $1.5 \times 10^4$ |
| B. mallei Δhcp1 | $1.5 \times 10^4$ |
| B. mallei ΔtonB Δhcp1 | $1.5 \times 10^4$ |

Infection Day 0
n = 11

Day 2
n = 3

————— Monitor Survival —————→

Day 21
Surviving animals

FIG. 19 hcp1 and tonB Mutants are Attenuated Compared to wt B. mallei

- Bm lux (1.5x10⁴ CFU)
- Bm ΔtonB (1.5x10⁴ CFU)
- Bm Δhcp1 (1.5x10⁴ CFU)
- Bm ΔtonB Δhcp1 (1.5x10⁴ CFU)

FIG. 20

**Single Vaccination With *B. mallei* Δ*tonB* Δ*hcp1* (1.5x10⁴ CFU) Generates Weak IgG Response**

| Vaccine (In dosage) | *B. mallei* specific IgG (ng/ml) |
|---|---|
| Bm Δ*tonB* (1.5x10⁴ CFU) | 16,481 ± ,6016.2 |
| Bm Δ*hcp1* (1.5x10⁴ CFU) | 6,035 ± 216.4 |
| Bm Δ*tonB* Δ*hcp1* (1.5x10⁴ CFU) | 75.6 ± 0.853 |
| PBS (50 μl) | N/D |

FIG. 21

Prime and Boost Vaccination Scheme With *B. mallei* Δ*tonB* Δ*hcp1* Produces Vigorous IgG Response

| Vaccine (1 ml dosage) | Number of doses | *B. mallei* Specific IgG (ng/ml) |
|---|---|---|
| Bm Δ*tonB* (1.5x10⁴ CFU) | Prime only | 16,481 ± 6,016.2 |
| Bm Δ*tonB* Δ*hcp1* (1.5x10⁴ CFU) | Prime and 2 boosts | 13,843.3 ± 2,666.4 |
| Bm Δ*tonB* Δ*hcp1* (1.5x10⁵ CFU) | Prime and 2 boosts | 15,581.1 ± 5,879.7 |
| PBS (50 µl) | Prime and 2 boosts | N/D |

FIG. 23

Organs from *B. mallei* Δ*tonB* Δ*hcp1* Prime and Boost Vaccinated Mice 35 Days Post Challenge are Unremarkable A. Δ*tonB* Δ*hcp1* ($1.5 \times 10^4$ CFU)

B. Δ*tonB* Δ*hcp1* ($1.5 \times 10^5$ CFU)

FIG. 26

**Bacteria Were Not Recovered from Organs of *B. mallei* Δ*tonB* Δ*hcp1* Vaccinated and wt Challenged Animals**

Lung Liver and Spleen Colonization

- Day 0
- Day 35    wt and Δ*tonB* Δ*hcp1* mutant

CFU/organ

Bm Δ*tonB* Δ*hcp1* 1.5×10⁴

Bm Δ*tonB* Δ*hcp1* 1.5×10⁵

FIG. 27

*B. mallei* Δ*tonB* Δ*hcp1* Addresses Cons Associated With Δ*tonB* Live Attenuated Vaccine

Pros

- 100% protection in acute inhalational models of murine glanders
- Wild type clearance
- Increases protective antibodies responses
- No evident gross pathology
- No evidence of inflammation
- Cellular responses and histopatholgy (PENDING)

Cons

- Persi✗tence
- Reversi✗n to wild type $Fe^{3+}$ → Δ*tonB*
*B. mallei*
Δ*hcp1*
Host Cells

FIG. 28

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: hcp1 Forward Primer

<400> SEQUENCE: 1
atgctggccg gaatatatct c                                          21

<210> SEQ ID NO 2
<211> LENGTH: 20

-continued

```
<212> TYPE: DNA
<213> ORGANISM: Artificial Sequence
<220> FEATURE:
<223> OTHER INFORMATION: hcp1 Reverse Primer

<400> SEQUENCE: 2
gccattcgtc cagtttgcgg                                                    20
```

ATTENUATED BURKHOLDERIA MALLEI STRAIN WHICH PROTECTS AGAINST PATHOGENIC BURKHOLDERIA INFECTIONS, VACCINE CONTAINING AND USE THEREOF

RELATED APPLICATIONS

This application claims priority to U.S. Provisional Application No. 62/338,630, filed May 19, 2016, which is incorporated herein by reference in its entirety.

SEQUENCE LISTING

The sequence listing file named "49561o1401.txt" having a size of 826 bytes and created Jul. 11, 2017, is hereby incorporated by reference in its entirety.

SEQUENCE LISTING

The sequence listing file named "49561o1401.txt" having a size of 826 bytes and created Jul. 11, 2017, is hereby incorporated by reference in its entirety.

FEDERAL FUNDING

The invention was funded by NIH grant US4A1057156 and RDIS 11-1-2-0075.

FIELD OF THE INVENTION

The invention generally relates to the development of an attenuated Burkholderia mallei strain and vaccine compositions containing this strain. These strains and vaccines containing may be used in humans and animals, e.g., equines, for treating or providing immunoprotection against infections elicited by category B, tier 1 pathogens, in particular Burkholderia mallei (Bm) and B. pseudomallei, which respectively are the causative agents of human glanders and melioidosis.

BACKGROUND OF THE INVENTION

There is an urgent need to develop effective therapeutic approaches against category B, tier 1 pathogens, such as Burkholderia mallei (Bm) and B. pseudomallei, the causative agents of human glanders and melioidosis. Concern over these bacteria has heightened because of the pathogens' seemingly perfect characteristics for malicious use as a biowarfare weapon against humans. A vaccine developed to combat these bacterial agents will also have value for the immunization of at-risk populations in melioidosis endemic areas of the world.

Burkholderia mallei are non-motile bacterium responsible for glanders. This disease mainly affects horses, which are considered to be the natural reservoir for infection, although mules and donkeys are also susceptible (Neubauer et al. 2005 Journal of Veterinary Medicine Series B 52:201-5). Humans are accidental hosts of B. mallei following prolonged and close contact with infected animals. B. mallei infect humans by entering through open wounds and surfaces of the eyes or nose. Symptoms of glanders are dependent on the route of infection (Srinivasan et al. 2001 N Engl J Med 345:256-8). B. pseudomallei are motile bacteria causing melioidosis (Dance 1991 Clin Microbiol Rev 4:52-60). Melioidosis is a life-threatening disease that is mainly acquired through skin inoculation or pulmonary contamination, although other routes have been documented. This saprophyte inhabitant of soil environments is mainly encountered in Southeast Asia and northern Australia, but is sporadically isolated in subtropical and temperate countries (Stone 2007 Science 317:1022-24).

Both Burkholderia species are highly pathogenic and are classified as such in list B by the Centers for Disease Control and Prevention (Horn 2003 Surgical Infections. 4:281-87). Burkholderia infections are difficult to treat with antibiotics and there are several reports that indicate it is feasible to protect against melioidosis, at least in animal models of disease, with non-living vaccines (Nelson et al. 2004 J Med Microbiol 53:1177-82). There has also been some progress in identifying partially protective subunits. Passively administered antisera raised against flagellin, polysaccharide, or conjugates of polysaccharide and flagellin, protect diabetic rats against challenge with B. pseudomallei (Brett et al. 1994 Infect Immun. 62:1914-19; Brett and Woods 1996 Infect Immun. 64:2824-28; Bryan et al. 1994 Can J Infect Dis. 5:170-78). However, B. mallei are not motile and do not produce flagella. Moreover, the ability of flagellin to induce protection against an aerosol, or intranasal challenge has not been reported. Therefore, flagellin was assessed as a potential candidate for inclusion in a Burkholderia vaccine and found unsuitable. In contrast, all of the current evidence indicates that other surface-expressed or secreted proteins are immunogenic and structural similarity exists between the proteins in B. pseudomallei and B. mallei (Whitlock et al. 2007 FEMS Microbial. Lett. 277:115-22; Whitlock et al. 2008 Transactions of the Royal Society of Tropical Medicine & Hygiene 102 Suppl: S127-33).

Burkholderia mallei, the causative agent of glanders, are Gram-negative, obligate mammalian pathogens. Glanders is primarily a disease of solipeds, with rare cases occurring among humans[1-2]. Naturally acquired human cases occur in endemic areas, particularly among those exposed to infected solipeds[2-4]. Additionally, cases have been reported among laboratory workers[5-6]. The World Organization for Animal Health coordinates ongoing efforts towards worldwide eradication; however, regional endemicity still exists in Africa, Asia, the Middle East, and South America[2]. Recent equid outbreaks in the Middle East and Asia[7-8-9] set the stage for possible glanders reintroduction into disease-free regions and as a result glanders is classified as a re-emerging disease.

Glanders is a debilitating and often fatal disease transmitted via cutaneous and respiratory routes. Disease course and severity is route-dependent, with respiratory cases being the most severe[3]. Respiratory infection is characterized by rapid onset of symptoms, including fever, lymphadenopathy, pulmonary abscesses, pneumonia, disseminated organ infection, and ultimately septicemia[3, 5, 10]. Because of the high incidence of septicemia following respiratory infection, fatality rates in human respiratory cases have been estimated at 90% without treatment and 40% with aggressive antibiotic therapy[11].

The use of B. mallei as a bio threat agent has been documented in different world military conflicts[10, 12-13]. Its amenability to aerosolization, low infectious dose, high case fatality rate, and high-level antibiotic resistance make B. mallei a top candidate for malevolent use[1, 10, 14]. Because of its perceived public health threat, the Department of Health and Human Services has categorized B. mallei as a Tier 1 Select Agent. The lack of effective treatments against these bacteria highlights the need for an effective vaccine. Numerous vaccine strategies have been tested; however, to date there are no approved vaccines and the search for a candidate that can provide sterilizing immunity has proven elusive.

Recently the subject inventors identified several proteins i.e., SimA, Hcp1 and BopA potentially capable of inducing a protective or therapeutic immune response to *Burkholderia mallei* or *B. pseudomallei*. (See U.S. Pat. No. 9,267,947, granted on Feb. 23, 2016). Notwithstanding the foregoing, other methods and compositions for use in protecting humans and animals (e.g., equine animals such as horses, donkeys, and mules) against the Gram-negative bacterial pathogens *Burkholderia mallei* and *B. pseudomallei* are desired.

The present invention addresses this need by providing novel attenuated *Burkholderia mallei* strains and vaccine compositions containing for use in treating and/or providing immunoprotection against infections elicited by *Burkholderia mallei* (Bm) and *B. pseudomallei*, especially human glanders and melioidosis.

SUMMARY OF THE INVENTION AND EXEMPLARY EMBODIMENTS

The present invention relates to novel attenuated *Burkholderia* vaccine strains which display reduced host persistence while maintaining the endogenous immunogenicity and protective properties.

In one embodiment the invention provides a live attenuated *Burkholderia* strain which contains at least 2 mutations which result in the deletion of all or part of tonB and hcp1 genes and/or the disruption in the expression or functionality of the gene product encoded by said tonB and hcp1 genes, wherein such live attenuated *Burkholderia* strain (i) elicits immunoprotection against *Burkholderia*, (ii) does not persist in vivo, and (iii) does not revert to the wild-type strain after administration to a susceptible host, e.g., an attenuated *Burkholderia mallei* (Bm) strain or *Burkholderia pseudomallei* (Bp) strain.

In some embodiments the live attenuated *Burkholderia* strain will comprise a mutation which reduces or eliminates the expression of tonB and hcp1.

In some embodiments the live attenuated *Burkholderia* strain will comprise mutations that delete of all or part of the coding sequences of said genes.

In some embodiments the live attenuated *Burkholderia* strain will comprise mutations that delete the promoters regulating the expression of both of said genes.

In an exemplary embodiment the live attenuated *Burkholderia* strain comprises a 162 base pair intragenic in-frame deletion in the hcp1 gene.

In a preferred exemplary embodiment the live attenuated *Burkholderia* strain comprises *B. mallei* ΔtonB Δhcp1 (CLH001) which strain has been deposited at The Biodefense and Emerging Infections Research Resources Repository (BEI Repository), 10801 University Boulevard, Manassas, Va. 20110-2209 (a National Institute of Allergy and Infectious Diseases (NIAID) program, managed by the American Type Culture Collection (ATCC)) or its progeny or a variant of *B. mallei* ΔtonB Δhcp1 (CLH001) e.g., one containing another attenuating gene mutation.

In another embodiment the invention provides an immunogenic composition comprising a live attenuated *Burkholderia* strain according to the invention and comprises at least one pharmaceutically acceptable carrier or excipient e.g., suitable for subcutaneous, inhalatory or intranasal administration, which optionally may be aerosolized or lyophilized.

In another embodiment the invention provides an immunogenic composition comprising a live attenuated *Burkholderia* strain according to the invention and further comprising an immune adjuvant, e.g., a TLR agonist, CD40 agonist, saponin, ALUM® or more specifically a TLR9 agonist such as a CPG oligodeoxynucleotide (CPG ODN).

In another embodiment the invention provides a method of eliciting an immune response, e.g., an antibody, TH1 response and/or a cellular immune response against *Burkholderia mallei* and/or *Burkholderia pseudomallei* in a subject in need thereof by administering a composition comprising a prophylactically or therapeutically effective amount of a live attenuated *Burkholderia* strain or immunogenic composition containing according to the invention.

In another embodiment the invention provides a method of treating or preventing glanders or melioidosis by administering a composition comprising a prophylactically or therapeutically effective amount of a live attenuated *Burkholderia* strain or immunogenic composition containing according to the invention.

In another specific embodiment the invention provides a method of eliciting an immune response, e.g., an antibody, TH1 response and/or a cellular immune response against *Burkholderia mallei* and/or *Burkholderia pseudomallei* by administering CLH001.

In another specific embodiment the invention provides a method of eliciting an immune response, e.g., an antibody, TH1 response and/or a cellular immune response against *Burkholderia mallei* and/or *Burkholderia pseudomallei* by administering at least $1.0 \times 10^2$, $1.0 \times 10^3$, $1.0 \times 10^4$, $1.0 \times 10^5$, or $1.0 \times 10^6$ CFU's of a live attenuated *Burkholderia* strain according to the invention to a subject.

In another specific embodiment the invention provides a method of eliciting an immune response, e.g., an antibody, TH1 response and/or a cellular immune response against *Burkholderia mallei* and/or *Burkholderia pseudomallei* in a human subject or an equine by administering a live attenuated *Burkholderia* strain according to the invention, e.g., CLH001, to an immunocompromised subject.

In another specific embodiment the invention provides a method of treating or preventing *Burkholderia* infection in a subject by administering a therapeutically or prophylactically effective amount of a live attenuated *Burkholderia* strain according to the invention, e.g., CLH001, or a vaccine or immunogenic composition containing to treat or prevent glanders or melioidosis

DESCRIPTION OF THE FIGURES

FIGS. 1A-G contains data showing that CLH001 is highly attenuated in BALB/c mice compared to CSM001 strain and exhibits increased safety over TMM001 and CLH002 strains at day 21 post infection. Panel (A) shows percent survival of BALB/c mice (n=8) following i.n. challenge with $1.5 \times 10^4$ CFU of CSM001 (●), TMM001 (■), CLH002 (♦), or CLH001 (▲) at 21 days post infection. Panel (B) (C) and (D) respectively show colonization of mouse lungs (B), livers (C), and spleens (D) (n=3) at day 2 (▲) and day 21 (■) post infection with $1.5 \times 10^4$ CFU of TMM001, CLH002, and CLH001. Panel (E) (F) and (G) respectively show that the limit of detection was 10 CFU/organ (horizontal dotted line). Comparison of histopathological scores for lungs (E), livers (F), and spleens (G) of PBS treated mice vs. mice infected with TMM001, CLH002, or CLH001 (n=3) at 21 days post infection.

FIGS. 2A-L contain representative images of organ pathology from challenged mice. H&E stained tissues displayed the types of pathology are seen in lungs (A-D), livers (E-H), and spleens (I-L) of mice challenged with PBS or $1.5×10^4$ CFU of TMM001, CLH002 or CLH001.

FIGS. 3A-D contains experimental results of experiments wherein NSG mice infected with CLH001 showed 100% survival and complete bacterial clearance. Panel (A) shows percent survival of NSG mice following i.n challenge with $1.5×10^4$ CFU of CSM001 (n=4, ●), or CLH001 (n=6, ▲) at 21 days post infection. Panel (B-D) respectively show the colonization of mouse lungs (B), livers (C), and spleens (D) (n=4) at day 21 post infection with $1.5×10^4$ CFU of CLH001 (■). The limit of detection was 10 CFU/organ (horizontal dotted line).

FIGS. 4A-D contain experimental results of prime and boost vaccination with CLH001 ($1.5×10^5$ CFU) showing that such vaccination provides 100% protection with no discernable organ colonization following CSM001 challenge. Panel (A) shows experimental results wherein mice were i.n. immunized with a prime and two boosts of PBS (n=8, ●), CLH001 at $1.5×10^4$ CFU (n=11, A) or $1.5×10^4$ CFU (n=11, A). Three weeks after receiving their second boost, mice were i.n. challenged with 1.5×10 CFU of CSM001. Panel (B-D) respectively show colonization of mouse lungs (B), livers (C) and spleens (D) (n=3/CLH001-vaccination group) at day 21 post-second vaccination boost (▲) and day 35 post-challenge with CSM001 (n=3 for CLH001 $1.5×10^4$ group and n=4 for CLH0001 $1.5×10^5$ group; ■). The limit of detection was 10 CFU/organ (horizontal dotted line).

FIGS. 5A-D contain experimental results of vaccination with CLH001 ($1.5×10^5$ CFU) demonstrating significant protection following B. mallei 23344 high dose challenge, but bacterial organ colonization was observed. In Panel (A) Mice were i.n. immunized with a prime and two boosts regimen of PBS (●) (n=8) or $1.5×10^5$ CFU CLH001 (▲) (n=11). Three weeks after last boost, mice were i.n. challenged with $3.5×10^5$ CFU of B. mallei 23344. Panel (B-D) respectively show the colonization of lungs (B), livers (C), and spleens (D) of CLH001-vaccinated mice at day 21 post-vaccination (▲) (n=3) and day 35 post-challenge (■) (n=4). The limit of detection was 10 CFU/organ (horizontal dotted line).

FIG. 6 contains experimental results demonstrating that CLH001 serum promotes killing of B. mallei 23344 in vitro. Serum bactericidal assays were performed by incubating $1.0×10^5$ B. mallei 23344 and guinea pig complement plus heat-inactivated naïve sera, heat-inactivated CLH001 sera, or anti-B. mallei LPS monoclonal antibody. After 6 h, samples were serially diluted and plated to determine CFU/ml. Experiments were performed in triplicate.

FIG. 9 contains experimental data showing that B. mallei ΔtonB attenuated virulence is partially rescued by iron supplementation.

FIG. 11 shows the gross pathology of B. mallei ΔtonB and PBS vaccinated mice 21 days post vaccination.

FIG. 12 contains experimental data showing that an aattenuated B. mallei ΔtonB protects against WT B. mallei challenge.

Figure 13:
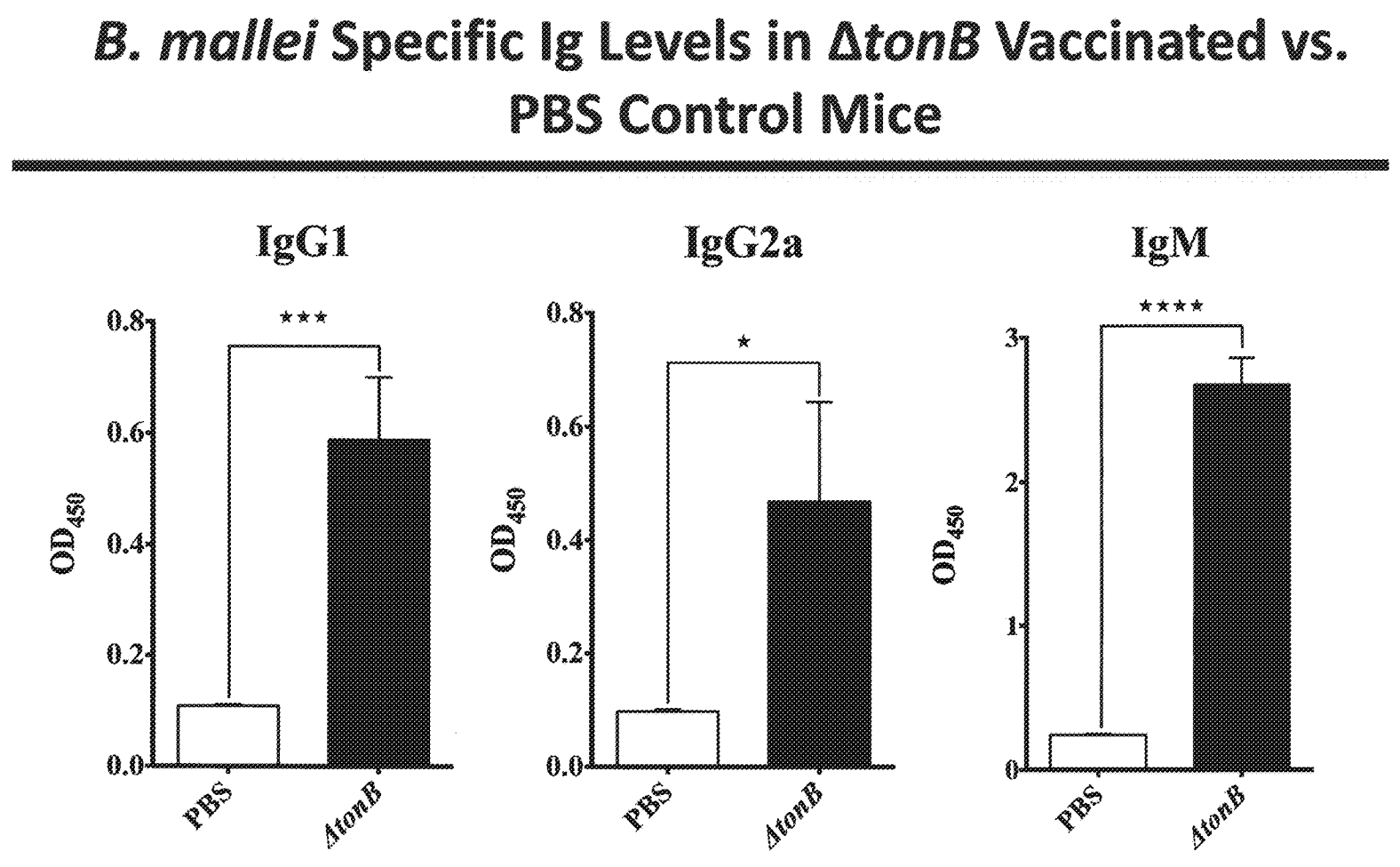

FIG. 13 contains experimental data showing B. mallei specific Ig Levels in ΔtonB Vaccinated vs. PBS Control Mice.

FIG. 14 contains histopathological data from B. mallei ΔtonB vaccinated vs. PBS control mice 48 h post-challenge.

FIG. 15 contains cytokine profiles of B. mallei ΔtonB vaccinated vs. PBS Control Mice 48 h Post Challenge.

FIG. 17 enumerates some advantages and disadvantages of B. mallei ΔtonB as a live attenuated vaccine.

Figure 18:
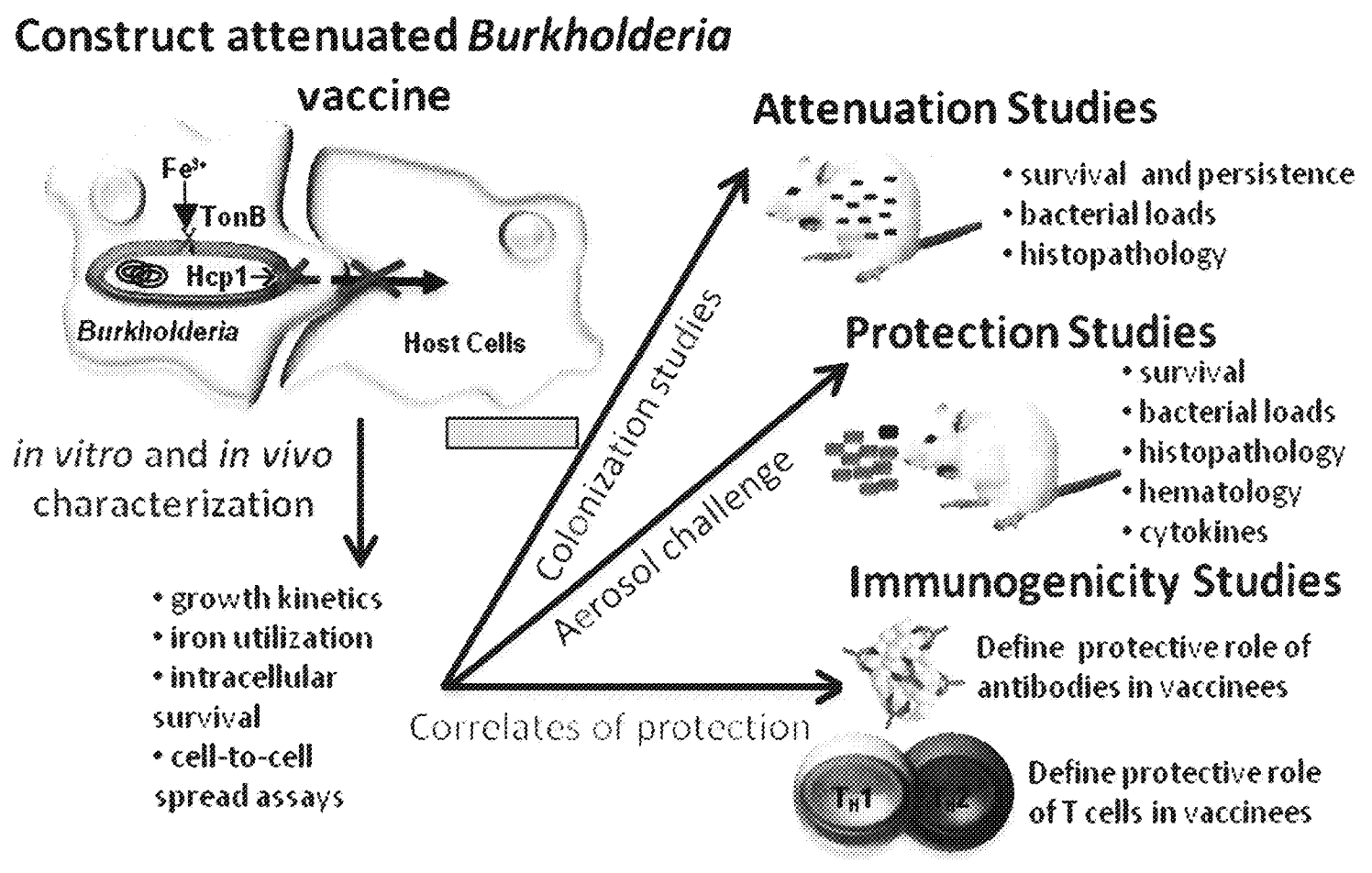

FIG. 18 schematically depicts the construction of an attenuated Burkholderia vaccine stain.

FIG. 19 compares B. mallei Δhcp1, ΔtonB and ΔtonB Δhcp1 survival and persistence over a 21 day period.

FIG. 20 compares the survival of B. mallei Δhcp1, ΔtonB and ΔtonB Δhcp1 to wild-type B. mallei.

FIG. 21 shows that a single vaccination with B. mallei ΔtonBΔhcp1 ($1.5×10^4$ CFU) generates a weak IgG Response.

FIG. 23 contains experimental data showing that this prime and boost vaccination protocol with B. mallei ΔtonBΔhcp1 elicited a vigorous IgG response.

FIG. 26 shows that organs obtained from B. mallei ΔtonB Δhcp1 prime and boost vaccinated mice 35 days post challenge are unremarkable.

FIG. 27 shows that bacteria were not recovered from organs of B. mallei ΔtonB Δhcp1 vaccinated and wt challenged animals.

FIG. 28 illustrates that B. mallei ΔtonB Δhcp1 alleviates the identified disadvantages of vaccines containing live attenuated ΔtonB 1 strains.

DETAILED DESCRIPTION OF THE INVENTION

Figure 7:
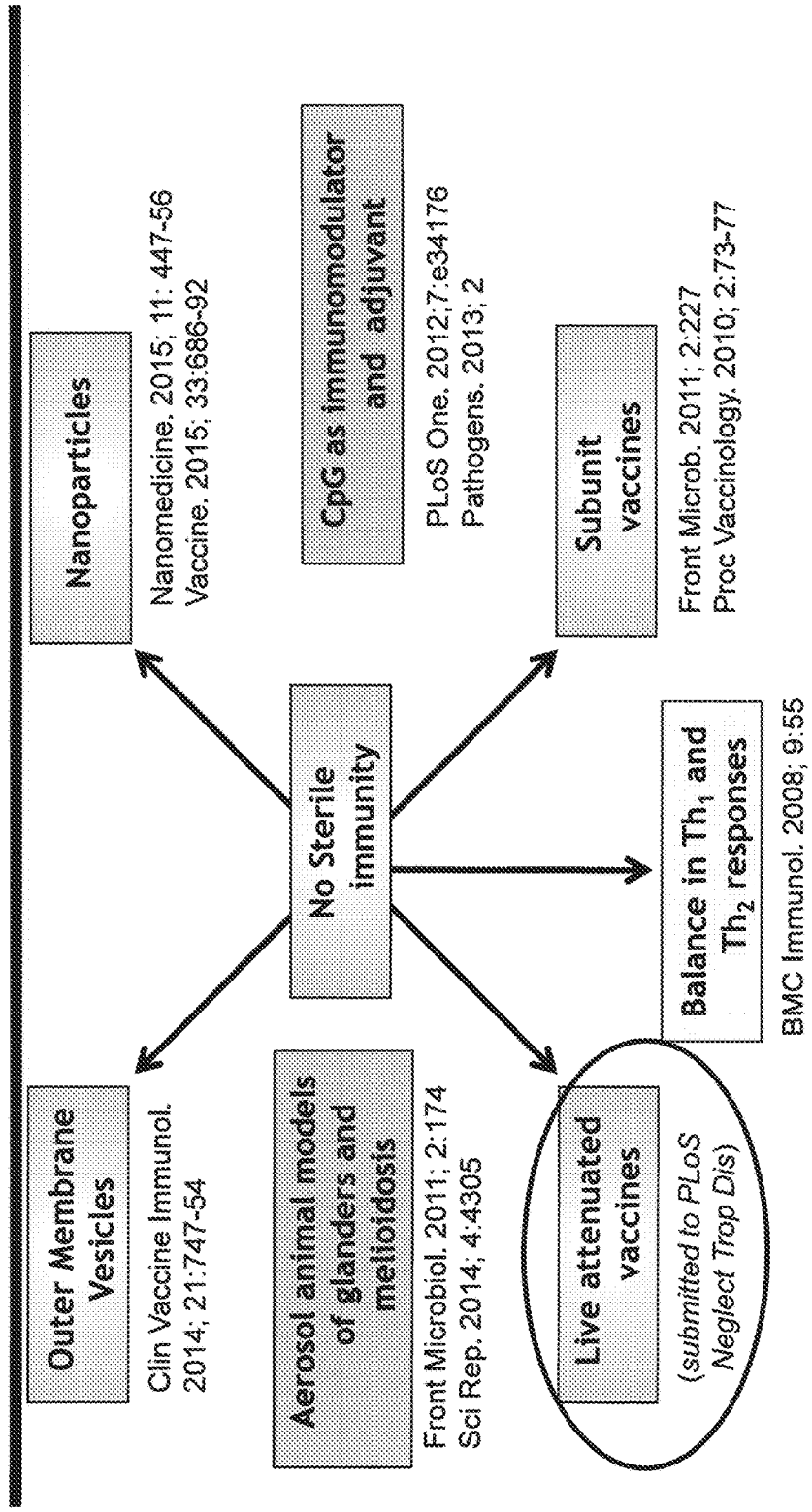
FIG. 7 schematically depicts a hholistic approach to developing Burkholderia vaccines.
Figure 8:
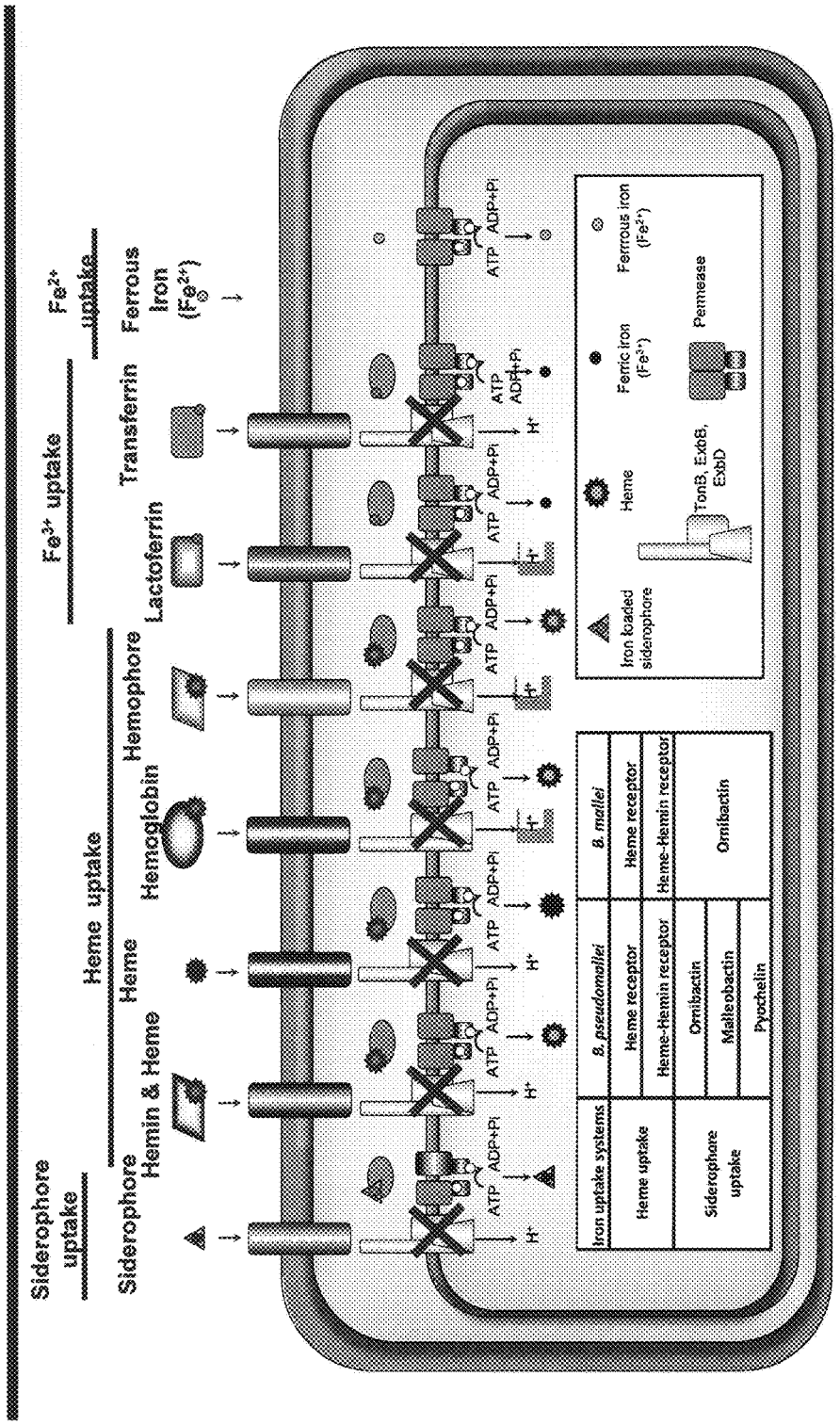
FIG. 8 summarizes some of the effects of TonB as an energizer of iron transport systems.
Figure 10:
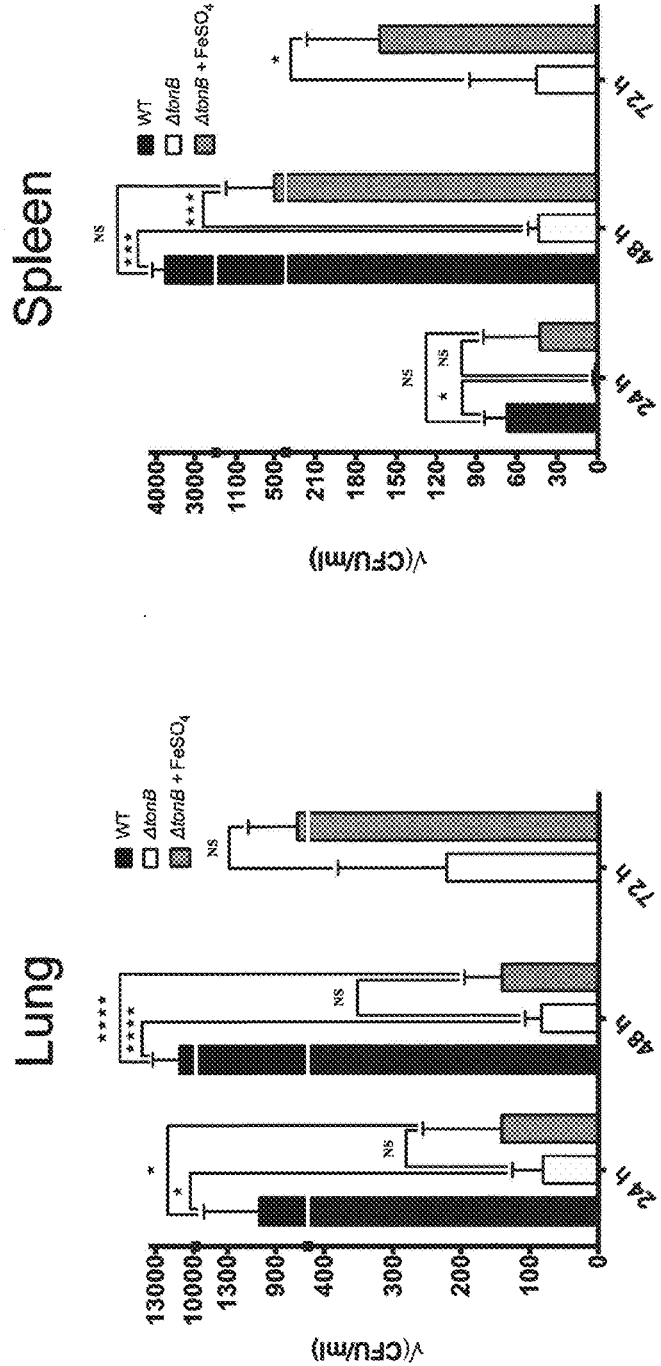
FIG. 10 contains experimental data showing that iron supplementation partially restores Stonb mutant's ability to colonize target organs.
Figure 16:
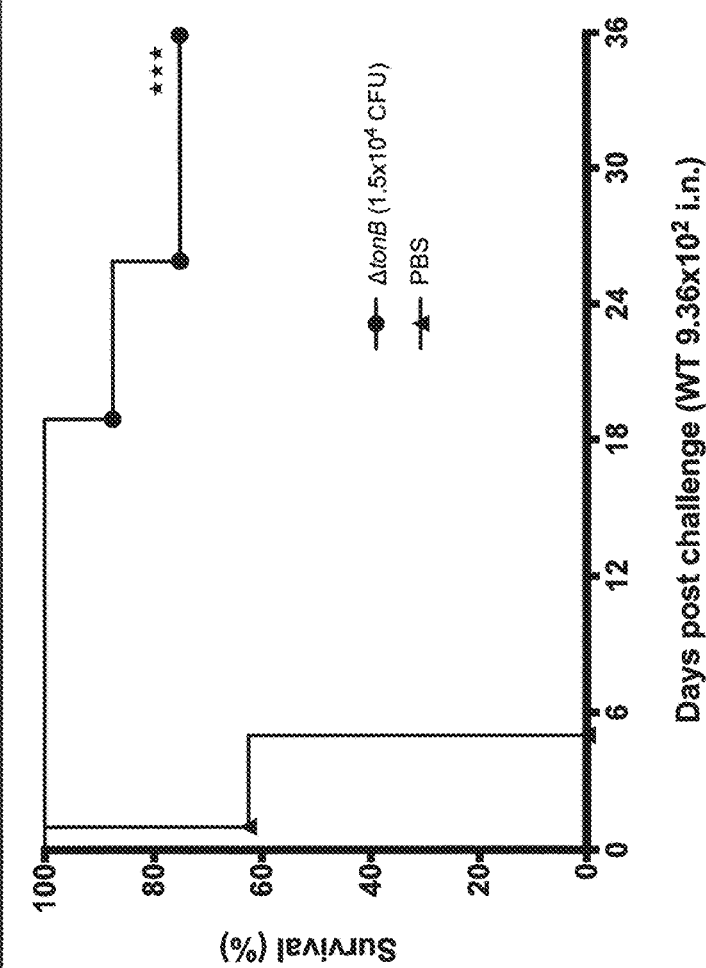
FIG. 16 contains experimental data showing that a B. mallei ΔtonB vaccine provides cross-protection against B. pseudomallei wild type challenge.
Figure 22:
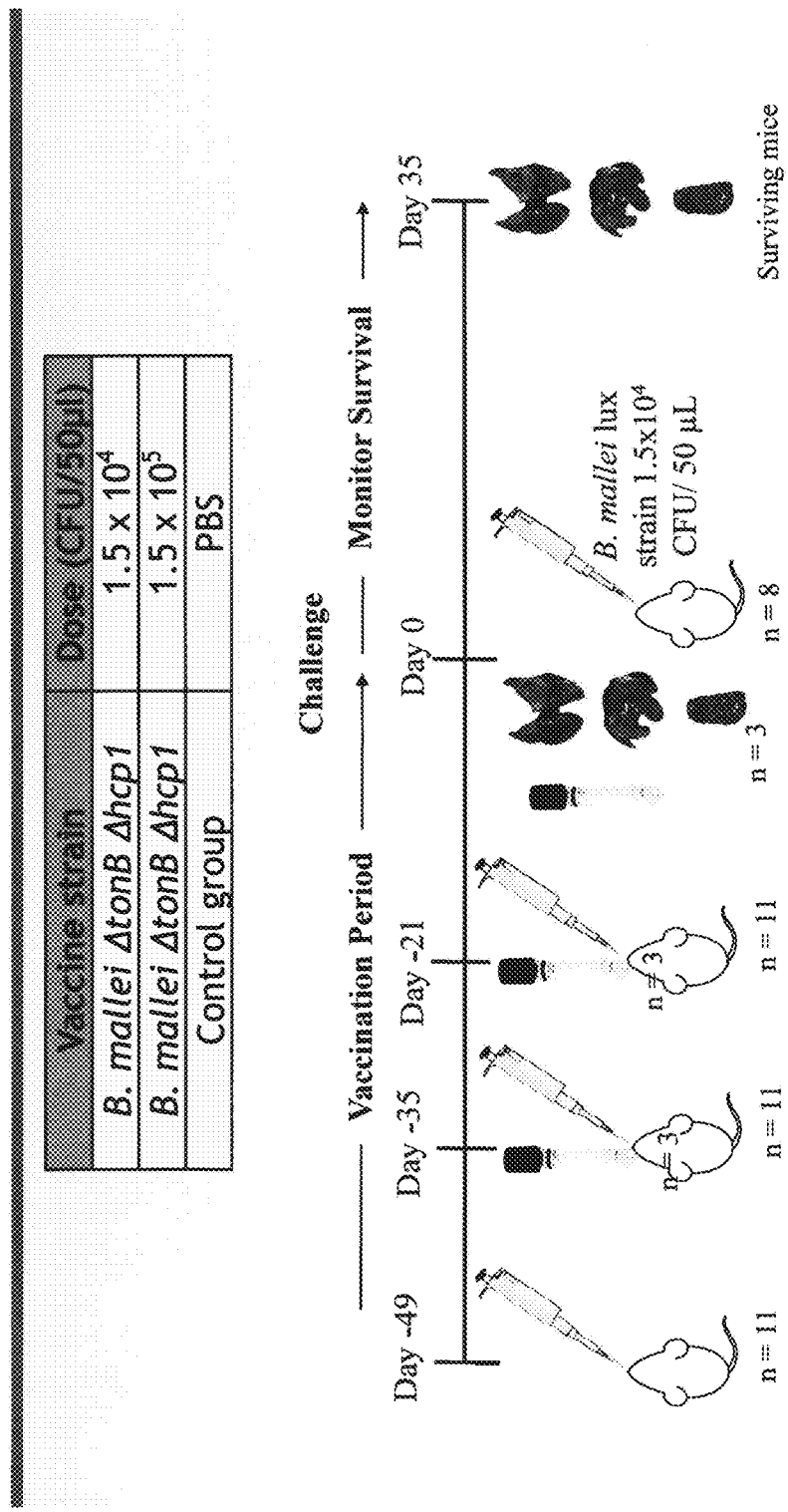
FIG. 22 outlines an intranasal prime and boost vaccination study protocol used herein.
Figure 24:
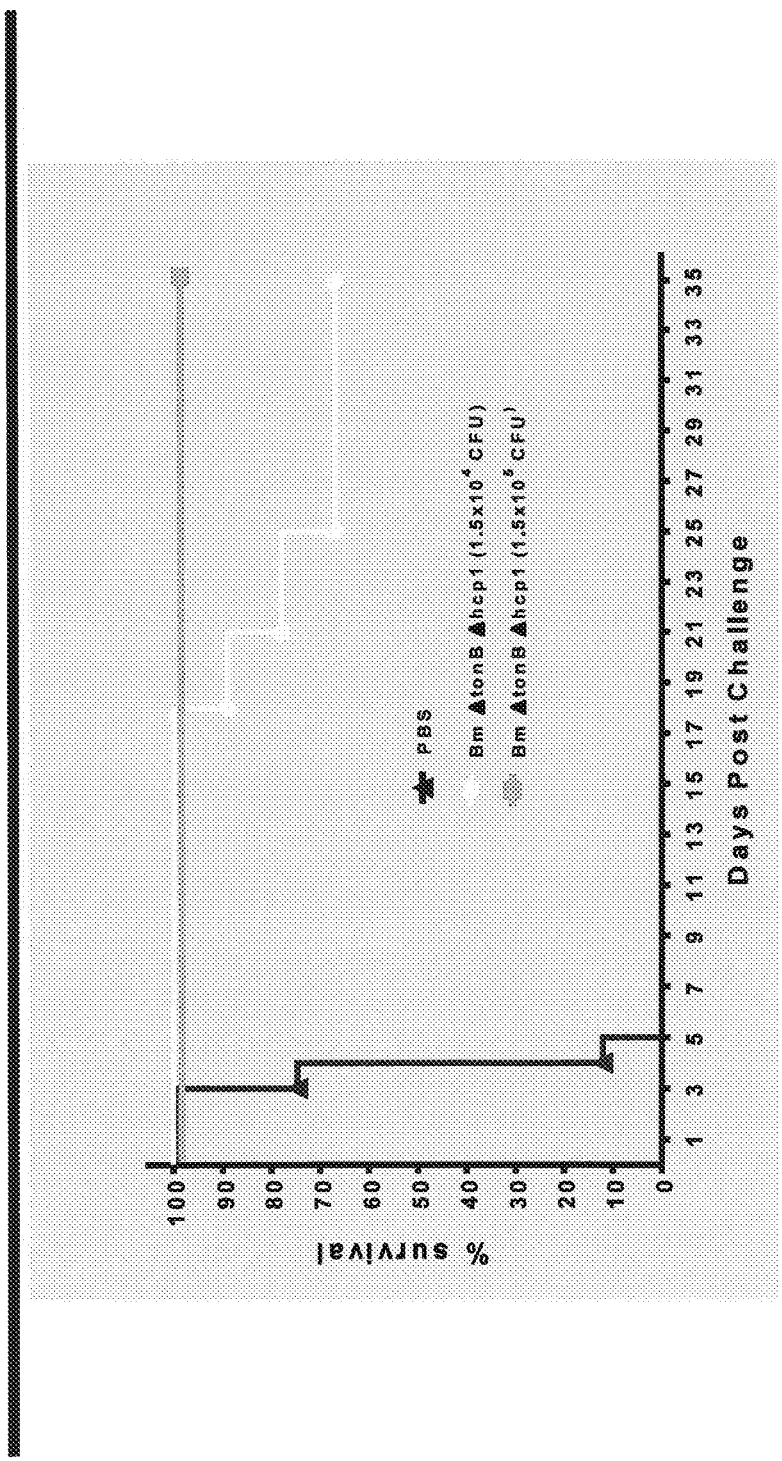
FIG. 24 contains experimental data showing that this prime and boost vaccination protocol with the B. mallei ΔtonBΔhcp1 mutant elicits protection against wt challenge.
Figure 25:
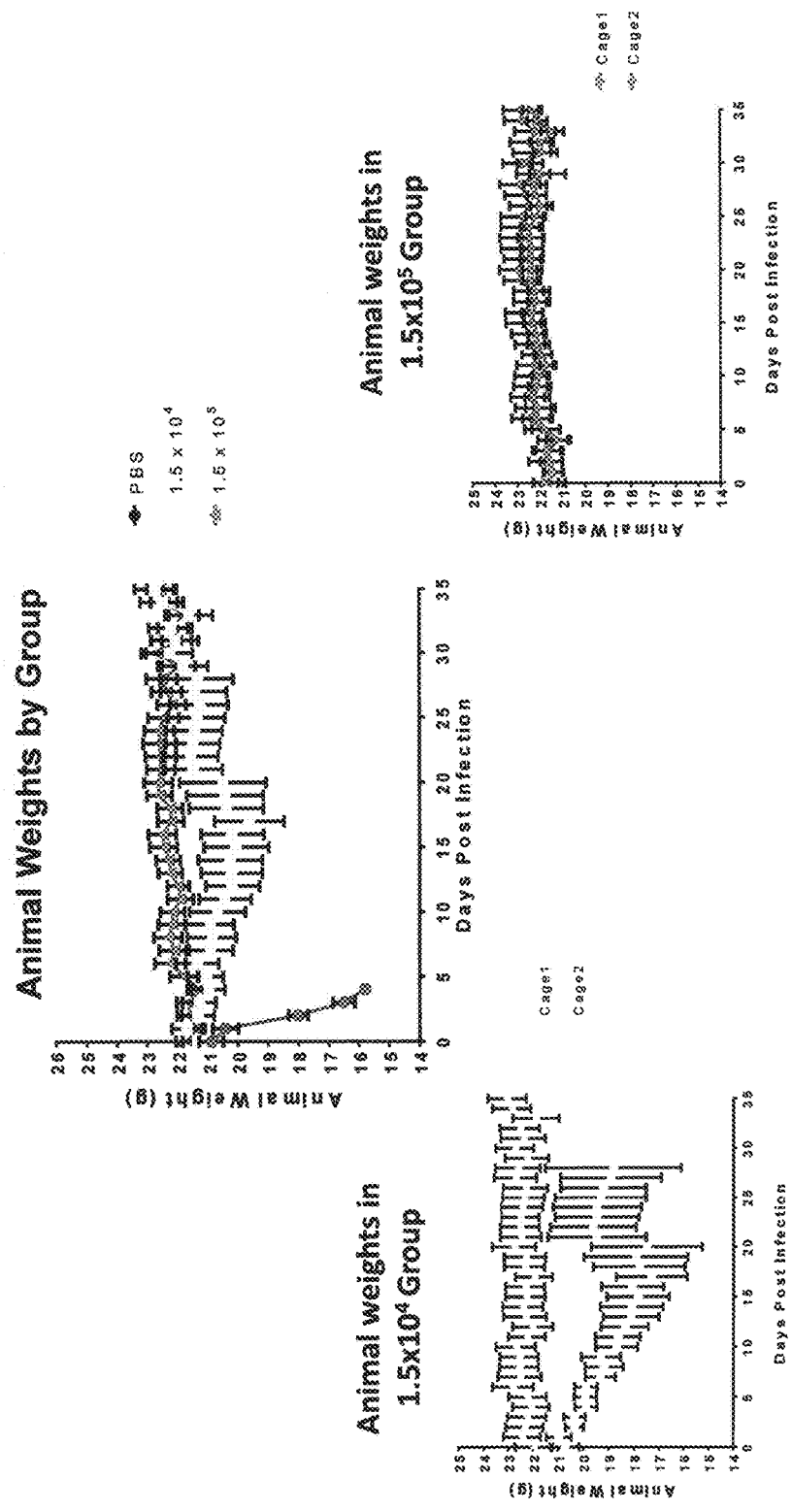
FIG. 25 contains experimental data showing that weights remain constant post-challenge in Bb. mallei ΔtonB Δhcp prime and boost vaccinated animals.

The present invention in general relates to the construction and characterization of novel attenuated Burkholderia vaccine strains which display reduced host persistence while maintaining the endogenous immunogenicity and protective properties. These stains and compositions containing may be used in treating or providing immunoprotection against infections elicited by category B, tier 1 pathogens, in particular Burkholderia mallei (Bm) and B. pseudomallei, the causative agents of human glanders and melioidosis, respectively.

Before describing the invention in further detain the following definitions are provided:

An "adjuvant" refers to a substance that enhances an immune response, e.g., an antibody or cell-mediated immune response against a specific agent, e.g., an antigen, or an infectious agent. Herein such adjuvant will especially include Toll-like receptor (TLR) agonists, e.g., TLR9 agonists such as a CPG oligodeoxynucleotide (CPG ODN) or other known adjuvants such as TLR agonists, CD40 agonists, saponin, and ALUM®.

An "attenuated" bacterial strain refers a mutated or modified or recombinant bacterium having reduced or no virulence or propensity to cause a disease or infection normally associated with the "wild-type" or unmodified bacterium.

An "attenuated" *Burkholderia* vaccine strain in particular refers to a *Burkholderia* bacterial strain which has been modified to have reduced or no virulence or propensity to cause a disease or infection which is normally associated with a "wild-type" or unmodified *Burkholderia* strain, in particular glanders or melioidosis. More particularly this includes "attenuated" *Burkholderia* vaccine strains which are mutated to delete all or part of tonB and hcp1 genes and/or disrupt the expression or functionality of the gene product encoded by said tonB and hcp1 genes, wherein such live attenuated *Burkholderia* strain (i) elicits immunoprotection against *Burkholderia*, (ii) does not persist in vivo, and (iii) does not revert to the wild-type strain after administration to a susceptible host.

"*Burkholderia*-associated infection" or "*Burkholderia* infection" herein refers to the infection of a susceptible host with a *Burkholderia* bacterium, e.g., *Burkholderia mallei* or *Burkholderia pseudomallei* and diseases associated therewith including in particular human glanders and melioidosis.

"Hemolysin-coregulated protein encoding gene" or "Hcp1" herein refers to a gene found in *Burkholderia* bacteria, e.g., *Burkholderia mallei* and *Burkholderia pseudomallei* strains which encodes a protein which is a substrate for the Type VI secretion system cluster 1, (T6SS1) and is postulated to comprise part of the T6SS secretion tube. This protein is involved in bacterial cell-to-cell spread.

"Reduced expression" of tonB and/or hcp1 herein means that a *Burkholderia* strain expresses less of the gene product encoded by the tonB and/or hcp1 genes relative to a corresponding wild-type or unmodified *Burkholderia* strain, e.g., it expresses at least 10, 20, 30, 40, 50, 60, 70, 80, 90, 95 or 99% less of the protein compared to a corresponding wild-type or unmodified *Burkholderia* strain, e.g., a *Burkholderia mallei* or *Burkholderia pseudomallei* strain.

Reduced "functionality" of the tonB and hcp1 genes means that the *Burkholderia* strain contains one or more mutations that inhibit or eliminate a function associated with the gene product encoded thereby.

"Reduced functionality of tonB" means that the *Burkholderia* strain contains one or more mutations which results in impaired function of the tonB gene product which is involved in iron utilization. Mutations which reduce or eliminate tonB function may be identified based on (i) reduced growth kinetics, siderophore hypersecretion and/or (iii) reduced utilization of heme-containing proteins as iron sources.

"Reduced functionality of hcp1" means that the *Burkholderia* strain contains one or more mutations which results in impaired function of the corresponding gene product which is a substrate for the Type VI secretion system cluster 1, (T6SS1) and is postulated to comprise part of the T6SS secretion tube. Therefore, mutations which result in reduced function of the hcp1 protein e.g., may be identified by screening for mutations in hcp1 which reduce or eliminate bacterial cell-to-cell spread.

"*Burkholderia mallei* ΔtonB Δhcp1" or "CLH001" herein refers to a specific attenuated "attenuated" *Burkholderia* vaccine strain containing deletion mutations which eliminate the expression of the tonB and hcp1 genes and which has been deposited at The Biodefense and Emerging Infections Research Resources Repository (BEI Repository).

A "variant" of *B. mallei* ΔtonB Δhcp1 or CLH001 herein refers to a CLH001 strain which has been modified in some manner, e.g., to include another genetic modification, e.g., another attenuating mutation or modification which further reduces virulence or infectivity such as the deletion or modification of another gene the expression of which may affect the persistence of the *Burkholderia* strain in a susceptible host or its virulence in a susceptible host.

An "immunogenic composition" herein refers to a composition containing an attenuated *Burkholderia* vaccine strain according to the invention which elicits an immune response in a susceptible host, e.g., an antibody, $T_h1$ or cellular (e.g., T cell-mediated) immune response.

A "vaccine" composition herein refers to a composition containing an attenuated *Burkholderia* strain according to the invention which elicits a therapeutic or prophylactic immune response against *Burkholderia*, preferably *Burkholderia mallei* or *Burkholderia pseudomallei*.

A "pharmaceutically acceptable carrier" or "excipient" refers to compounds or materials conventionally used in immunogenic or vaccine compositions during formulation and/or to permit storage.

"Intranasal composition" or "inhalatory composition" or "aerosol composition" herein refers to a composition containing an attenuated *Burkholderia* vaccine strain according to the invention which is suitable for intranasal or aerosol delivery.

"Prophylactically effective amount" of a live attenuated *Burkholderia* strain according to the invention refers to an amount sufficient to prevent or reduce the incidence of infection in a susceptible host.

"Therapeutically effective amount" of a live attenuated *Burkholderia* strain according to the invention refers to an amount sufficient to treat *Burkholderia* infection or a disease associated therewith in a susceptible host.

A "susceptible host" herein refers to a host or animal that may be infected by *Burkholderia*, in particular *Burkholderia mallei* or *Burkholderia pseudomallei*. Such hosts include humans or non-human primates and equines, e.g., horses, donkeys and mules.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as an isolated bacterium or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter. The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Having provided the foregoing definitions, the invention is now further described.

The invention generally relates to the development of an attenuated *Burkholderia* strain and immunogenic or vaccine compositions containing this strain. These strains and immunogenic compositions or vaccines containing may be used in humans and animals, e.g., equines, eliciting an immune response and for treating or providing immunoprotection against infections elicited by category B, tier 1 pathogens, in particular *Burkholderia mallei* (Bm) and *B. pseudomallei*, which respectively are the causative agents of human glanders and melioidosis.

These attenuated bacterial strains may e.g., be created by engineering mutations which eliminate or reduce the expression of the *Burkholderia mallei* or *pseudomallei* hcp1 and tonB genes or which impair functionality of the corresponding gene products. In an exemplary embodiment a mutated *Burkholderia mallei* strain referred to as "*Burkholderia mallei* ΔtonB Δhcp1" or "CLH001" is obtained which comprises deletion mutations which remove hcp1 and tonB gene sequences which deletions eliminate the expression of the tonB and hcp1. This attenuated strain is exemplary of the invention and the synthesis of this strain is embodied in the working examples.

Other *Burkholderia mallei* or *pseudomallei* mutants may be obtained by use of conventional methods for introducing gene mutations or deletions which are designed to reduce or eliminate gene expression. For instance, attenuation may be accomplished by altering (e.g., deleting) native tonB and hcp1 nucleic acid sequences found in the wild type bacterium. Methods for introducing targeted deletions or insertions that result in gene inactivation are well known in the art such as site-specific mutagenesis, homologous recombination, and the use of suicide vectors. Also, in some embodiments, the bacterium may also comprise a mutation in a transcription factor as a means to further attenuate the bacterium.

Appropriate known methods include cloning the DNA sequence of the wild-type gene into a vector, e.g. a plasmid, and inserting a selectable marker into the cloned DNA sequence or deleting a part of the DNA sequence, resulting in its inactivation. Alternatively attenuating mutations that eliminate or reduce hcp1 and tonB may be introduced using suicide vectors (see e.g., Sambrook, J., E. F. Fritsch, and T. Maniatis, *Molecular cloning: a laboratory manual*. 2nd ed. 1989: Cold Spring Harbor Laboratory Press, Cold Spring Harbor, N.Y.

A deletion may be introduced by, for example, cutting the DNA sequence using restriction enzymes that cut at two points in or just outside the coding sequence and ligating together the two ends in the remaining sequence. Alternatively, a mutant allele in which the flanking regions of a target gene are amplified separately and linked directly together in a separate overlap PCR reaction, with omission of the intervening target sequence, can be constructed (see, e.g., Turner, A. K., et al., Construction and characterization of genetically defined aro omp mutants of enterotoxigenic *Escherichia coli* and preliminary studies of safety and immunogenicity in humans. *Infect Immun*, 2001. 69(8): p. 4969-79.) A plasmid carrying the mutated DNA sequence can be transformed into the bacterium by known techniques such as electroporation and conjugation. It is then possible by suitable selection to identify a mutant wherein the inactivated DNA sequence has recombined into the chromosome of the bacterium and the wild-type DNA sequence has been rendered non-functional by homologous recombination.

Furthermore, antibiotic resistance genes must generally be removed from the bacteria before they are used in a vaccine or immunogenic composition. Bacteria isolated from the wild often contain antibiotic resistance genes, e.g., those which confer resistance against ampicillin, streptomycin, sulphmethoxazole, kanamycin, trimetheprim and tetracyclin. These genes can be removed by methods known to those skilled in the art.

Attenuated bacteria produced according to the invention will be used to confer prophylactic or therapeutic protection in susceptible hosts in order to treat or prevent *Burkholderia* infection, e.g., to treat or prevent glanders and melioidosis.

In a preferred exemplary embodiment the inventors have developed iron uptake deficient (ΔtonB) and cell-to-cell spread defective (Δhcp1) *B. pseudomallei* (Bpm) and *B. mallei* (Bm) attenuated strains, which strains were characterized and evaluated in order to determine if these putative attenuated *Burkholderia* strains possessed reduced persistence and enhanced protective properties. Specifically, this was effected in acute inhalational infection models of murine glanders and melioidosis. The hope was that the obtained attenuated Bm vaccine strains would be determined to be safe and effective, and further that this strain would be suitable for "scaling up", i.e., these strains may be readily reproduced facilitating the manufacture of multiple (hundreds, thousands or more) of vaccine doses as might be required in an epidemic scenario. Moreover, the challenge was identifying a vaccine strain that eliminates persistence but which is still sufficiently immunogenic, i.e., the strain when administered to a susceptible host, i.e., a human or non-human animal, is capable of affording complete protection against a lethal challenge with either *Burkholderia* strains.

As shown herein, these objectives were achieved and indeed the present invention provides a vaccine that can confer sterilizing immunity and long term protection against *Burkholderia* infections. Specifically, as described in detail infra, an attenuated Bm strain was tested for its protective properties in clinically relevant models of infection and the data demonstrated that a Bm tonB hcp1 double mutant vaccine strain referred to herein as CLH001 did not persist while eliciting protective immunity against melioidosis and glanders. Further, the safety and efficacy of the CLH001 (*B. mallei* ΔtonB Δhcp1 mutant) vaccine strain was further evaluated in NOD SCID γ mice (immunocompromised mice). Based on the observed safety and efficacy profile this strain should be well suited for use as a live attenuated vaccine for treating or conferring immunoprotection against both types of *Burkholderia* strains.

Live attenuated vaccines, which are regarded as the most viable strategy against *B. mallei*, have been tested with some success[14-17]. Recently, the present inventors evaluated an iron acquisition-deficient *B. mallei* ΔtonB (TMM001) strain, as a live attenuated vaccine in an acute inhalational glanders and melioidosis (*B. pseudomallei*) murine models. BALB/c mice intranasal (i.n.) vaccinated with TMM001 at $1.5 \times 10^5$ and $1.5 \times 10^4$ CFU doses and i.n. challenged with $1.5 \times 10^4$ CFU of *B. mallei* lux strain CSM001 had survival rates of 100% and 75%, respectively. Necropsy and organ CFU enumeration showed that all mice had splenomegaly and splenic abscesses due to TMM001 colonization[18]. This study is significant because it represents the first attenuated strain to provide 100% and 75% survival against *B. mallei* and *B. pseudomallei* challenge, respectively. However, the persistence of TMM001 poses a significant safety concern. In an effort to achieve increased safety while still maintaining protection, we utilized the TMM001 strain as a platform for additional gene deletion.

Type six secretion systems (T6SSs) are highly conserved among Gram-negative bacteria[19]-[20] and the essential role of the T6SS cluster 1 (T6SS-1) genes were demonstrated in the virulence of *B. mallei* using rodent models of infection[21]. Further, the T6SS-1's hemolysin coregulated protein (Hcp1) serves as both a structural component and a secreted protein, which plays important role in T6SS-1 function and *B. mallei* pathogenesis[19, 21, 22]. Deletion of the T6SS apparatus components (including the hcp1 gene) resulted in *B. mallei* and *B. pseudomallei* mutants that exhibited significant impairment in intracellular growth, intracellular spread and multinucleated giant cell (MNGC) formation[22-,23]. MNGC formation is characteristic of *B. mallei* and *B. pseudomallei* infections and has been detected in eukaryotic cell culture as well as in animal models of infection[22, 24-25]. MNGCs are believed to be involved in these organisms' ability to establish persistent infections by allowing intracellular spread and immune evasion[1, 23, 26]. We predicted that deletion of both *B. mallei* hcp1 and tonB genes would produce a strain more susceptible to host clearance, resulting in a safer, yet fully protective vaccine.

To assess the in vivo attenuation of mutant strains, BALB/c mice were challenged with $1.5 \times 10^4$ CFU of *B. mallei* ΔtonB (TMM001), Δhcp1 (CLH002), ΔtonB Δhcp1 (CLH001) or highly virulent *B. mallei* lux (CSM001)[27]. All the animals infected with the CSM001 succumbed to infection by day 3 post-challenge. In contrast, all mice receiving TMM001, CLH002, or CLH001 survived to the end of the study (****, p<0.0001) (FIG. 1A). At days 2 and 21 post-challenge, the lungs, spleens and livers were removed, homogenized and plated for CFU enumeration. At day 2 post-challenge, the CFU counts in organs from TMM001-, CLH002- and CLH001-infected mice were greatly reduced compared to those from CSM001-infected mice (FIG. 1B-D). At day 21 post-challenge, bacteria were not recovered from the lungs and livers of TMM001-, CLH002- and CLH001-infected mice (FIG. 1B-C). As previously observed, high CFU numbers were recovered from the spleens of TMM001-infected mice (FIG. 1D and [18]). In contrast, lower numbers of bacteria were recovered from the spleens of CLH002-infected mice and no bacteria were recovered from the spleens of mice receiving CLH001.

Histopathological analysis of the tissues (lungs, livers, and spleens) of mice challenged with the different strains was compared to PBS-treated BALB/c mice (FIG. 2A-L). The organs of TMM001-infected mice presented with mild to moderate pathologic changes, including mild perivascular and peribronchial inflammatory infiltrates in the lung sections (FIG. 2B), foci of mild hepatocellular necrosis (FIG. 2F), and mild to moderate necrosis of follicles were visible in the spleen (FIG. 2J). While the TMM001 organs generally exhibited increased abnormal findings relative to similar organs from the other treatment groups, only their spleens exhibited significant changes in histopathology compared to spleens from PBS-treated mice (*, p=0.02) (FIG. 1G) and minimal pathologic changes were noted in lungs and livers (FIGS. 1E and F). Overall, reduced pathologic changes were noted in CLH002-challenged mice compared to TMM001-infected mice. The lungs of CLH002-challenged BALB/c mice were considered mostly unremarkable (FIG. 2C), but the livers and spleens exhibited small foci of necrosis (FIGS. 2G and K). In contrast, organs of mice vaccinated with CLH001 mutant were unremarkable and resembled organs from PBS-treated mice. (FIGS. 2D, H, and L).

We further evaluated the safety of our CLH001 vaccine in NOD.Cg-Prkdc$^{scid}$Il2rg$^{tm1Wjl}$/SzJ or NOD SCID gamma (NSG) mice. The NSG mice are considered the most highly immunodeficient mouse available and such immunodeficiency provides a practical model to test vaccine-associated morbidity and mortality. NSG mice challenged i.n. with $1.5 \times 10^4$ CFU of CSM001 or CLH001 were used to evaluate persistence and/or dissemination to target organs. All mice challenged with CSM001 (n=4) succumbed to infection by day 3 post-challenge. In contrast, mice receiving CLH001 (n=6) survived to the end of the study (**, p=0.0027) (FIG. 3A). At 21 days post-challenge, the organs of surviving mice were evaluated for CFU and no bacteria were detected in the lungs, livers, or spleens (FIGS. 3B, C and D, respectively) of any of the mice. Gross pathology and histology analysis of these organs indicated that the architecture was unremarkable compared to organs from an uninfected NSG mouse (data not shown).

Next, we evaluated whether CLH001 vaccination was protective against a lethal dose of CSM001. Mice received a prime and two boost vaccination (14 days apart) with $1.5 \times 10^4$ or $1.5 \times 10^5$ of CLH001. Sera was collected from mice (n=3) at two week intervals following each prime and boost dose, and compared to serum from TMM001-vaccinated mice. *B. mallei*-specific IgG, IgG2a, and IgG1 reciprocal endpoint titers were determined via indirect ELISA. A retrospective analysis of serum from TMM001-vaccinated mice found that the vaccine generated a strong *B. mallei*- specific IgG response (mean reciprocal endpoint titer=51,200±0) with a Th1-bias (IgG2a:IgG1 ratio=4.4) (See Table 1 below).

TABLE 1

Serum antibody response of BALB/c mice i.n. vaccinated with live attenuated *B. mallei* attenuated strains

| Vaccine/Dosage (P, B, or 2B)[a] | Serum titer[b] | | | Serum ratio |
|---|---|---|---|---|
| | IgG | IgG2a | IgG1 | IgG2a/IgG1 |
| PBS | ND[c] | ND | ND | — |
| TMM001/1.5 × 10$^4$ CFU (P) | 51,200 ± 0 | 136,533 ± 48,272 | 31,289 ± 14,504 | 4.4 |
| CLH001/1.5 × 10$^4$ CFU (P) | 400 ± 0 | ND | ND | — |
| CLH001/1.5 × 10$^5$ CFU (P) | 3,733 ± 2,325 | 944 ± 163 | ND | — |
| CLH001/1.5 × 10$^4$ CFU (B) | 4,267 ± 2,133 | 5,511 ± 473 | 1,422 ± 154 | 3.9 |
| CLH001/1.5 × 10$^5$ CFU (B) | 19,200 ± 7,692 | 31,259 ± 7,853 | 8,533 ± 1,742 | 3.7 |
| CLH001/1.5 × 10$^4$ CFU (2B) | 19,911 ± 5,321 | 18,489 ± 6,517 | 8,533 ± 3,695 | 2.2 |
| CLH001/1.5 × 10$^5$ CFU (2B) | 42,667 ± 6,967 | 96,711 ± 8,533 | 24,178 ± 2,011 | 4 |

[a]Antibody titers were determined at 3 weeks post primary vaccination (P) and 3 weeks post boost (B). PBS Control animals were vaccinated with 50 µl of PBS. TMM001 vaccinated animals (prime only) were included for comparison.
[b]To determine serum antibody titers, sera from 3 mice/group were tested by indirect ELISA with irradiated *B. mallei* ATCC 23344 whole cells used as the antigen. Titers were performed in triplicate and reported as the mean reciprocal endpoint titer ±S.D.
[c]Not detected, because titers less than or equal to 100 were considered to be negative.

As hoped, CLH001-vaccinated mice developed an anamnestic response to all antibodies tested following each subsequent CLH001 vaccination at both doses. The CLH001 (1.5×10$^5$ CFU) prime and two boosts sera had the highest *B. mallei*-specific IgG total value for this vaccine and gave similar values to those seen in TMM001-vaccinated mice. Further, the observed ratio of IgG2a:IgG1≥4.0 has also been described as being favorable for protection (Table 1). The prime and two boosts vaccinated BALB/c mice (PBS, 1.5×10$^4$ or 1.5×10$^5$ CFU CLH001) were challenged with 1.5×10$^4$ CFU of CSM001. All PBS-treated mice succumbed to infection by day 5 post-challenge; however, animals vaccinated with both CLH001 doses exhibited survival of 62.5% (*, p<0.0002) and 100% (**, p<0.0001), respectively, at the 35 day experimental end point (FIG. 4A).

Organs were collected 21 days post-vaccination and 35 days post-challenge for CFU enumeration. Bacteria were not detected in the lungs, livers, or spleens (FIGS. 4B, C and D, respectively) of any of the mice tested. Additionally, gross pathology and histology analysis of these organs indicated that the architecture was mostly unremarkable compared to organs from PBS-treated uninfected mice (FIG. 27).

Next, we evaluated whether CLH001 was protective against high dose challenge with *B. mallei* wild type strain ATCC 23344. BALB/c mice were prime and boosted twice (14 days apart) with PBS or 1.5×10$^5$ CFU of CLH001, and challenged with 3.5×10$^5$ CFU of *B. mallei* 23344 at 21 days after the last vaccine boost. *B. mallei*-specific IgG, IgG2a, and IgG1 reciprocal endpoint titers from sera collected two weeks following each vaccination closely mimicked those seen in the previous prime and boosts vaccination experiment. All PBS-treated mice succumbed to infection, and survival was maintained at 87.5% (****, p<0.0001) in CLH001-vaccinated mice until the experimental endpoint (FIG. 5A). Although bacteria were not detected from the lungs, livers, or spleens (FIGS. 5B, C and D, respectively) of any of the mice at day 21 post-vaccination, or the lungs (FIG. 5B) at day 35 post-challenge, significant bacterial counts were recovered in two of the livers (4.97×10$^4$ and 1.28×10$^5$ CFU/organ) (FIG. 5C) and all of the spleens (mean=3.5×10$^8$ CFU/organ) (FIG. 5D).

The correlation between higher *B. mallei*-specific antibodies in animals vaccinated with CLH001 at 1.5×10$^5$ CFU and increased survival rates led us to hypothesize that antibodies likely play an important role in protection. Therefore, we performed a serum bactericidal assay to evaluate whether antibodies from CLH001-vaccinated mice were able to reduce bacterial burden. *B. mallei* ATCC 23344 was incubated in LBG media containing guinea pig complement and one of the following: heat-inactivated naïve sera, heat-inactivated CLH001 sera, or anti-*B. mallei* LPS monoclonal antibody (anti-LPS mAb). The number of bacteria grown in the presence of naïve serum indicated nearly a six-fold increase over the initial bacterial concentration; meanwhile, the number of bacteria grown in the presence of CLH001 sera or anti-LPS mAb decreased below the initial bacterial concentration and contained significantly less bacteria than the naïve sera culture (**, p=0.0062 and p=0.0063 for these groups respectively) (FIG. 6).

The experimental details of these experiments are described in more detail in the following examples. These examples are offered to illustrate, but not to limit, the claimed invention.

EXAMPLES

Example 1: Bacterial Strains and Growth Conditions

*E. coli* were grown in Luria-Bertani (LB) media at 37° C. All manipulations of *B. mallei* strains were conducted in CDC-approved and registered biosafety level 3 (BSL3) or CDC/USDA-approved and registered animal biosafety level 3 (ABSL3) facilities at the University of Texas Medical Branch and experiments were performed in accordance with Select Agent standard operating practices. *B. mallei* strains were taken from freezer stocks, plated on LB agar containing 4% glucose (LBG) and 200 µM FeSO$_4$ and incubated 37° C. for 3 days. For liquid cultures, 2-3 colonies were inoculated into 20 mL of LBG broth. Liquid cultures were then incubated overnight (18 h) at 37° C. with agitation (200 rpm). Challenge and vaccination doses were prepared from overnight LBG cultures and diluted in phosphate buffered saline (PBS) in a total volume of 50 µL (25 µL/nare).

Example 2: Construction of *B. mallei* ΔHcp1 and ΔtonB ΔHcp1 Mutants

Construction of the *B. mallei* Δhcp1 (CLH001) and ΔtonB Δhcp1 (CLH002) mutants were developed using a donor strain and plasmid strain donated by Dr. Mary Burtnick (University of South Alabama). The donor strain was a chemically competent *E. coli* S17-1 λpir strain containing a pMo 130ΔNX plasmid designed to introduce a 162 base pair intragenic in-frame deletion in the hcp1 gene 23. The CLH002 mutant was created by introducing the plasmid from the donor strain into *B. mallei* 23344 via bi-parental mating. Deletion mutants were isolated by selection on kanamycin (Km) agar plates, followed by counter selection on 5% sucrose YT agar supplemented with 200 μM FeSO4. The CLH001 mutant was created by introducing the plasmid into *B. mallei* TMM001 via conjugal transfer and repeating the screening and confirmation process as described above. The Δhcp1 mutation was then confirmed via PCR amplification, followed by sequencing, of the hcp1 gene using the following primers: Forward primer SEQ ID NO:1 (ATG CTG GCC GGA ATA TAT CTC); Reverse primer SEO ID NO:2 (GCC ATT CGT CCA GTT TGC GG).

Example 3: Animal Studies

All animal experiments were performed using female, 6- to 8-week-old, BALB/c mice or NOD.Cg-Prkdc$^{scid}$ Il2rg$^{tm1Wjl}$/SzJ (NSG) mice obtained from Charles River (Wilmington, Mass., USA). Mice were housed in microisolator cages under pathogen-free conditions, provided with rodent feed and water ad libitum, and maintained on 12 h light cycle. To allow adequate acclimation, mice were housed within the animal facility for 1 week prior to experimentation. This study was carried out in strict accordance with the recommendations in the *Guide for the Care and Use of Laboratory Animals* of the National Institutes of Health. The protocol was approved by the Animal Care and Use Committee of the University of Texas Medical Branch (Protocol Number: 0503014B).

Example 4: Survival Study

Anesthetized BALB/c mice (n=11) were challenged i.n. with 1.5×10$^4$ CFUs of *B. mallei* luminescent reporter strain (CSM001) or isogenic mutants TMM001, CLH002, or CLH001. At day 2 post-infection, mice (n=3) were euthanized and their lungs, livers, and spleens were aseptically harvested for CFU enumeration. The remaining BALB/c mice (n=8) were monitored for survival for 21 days. Survival curves were generated and analyzed using the Kaplan-Meier method and a significant difference in survival curves was ascertained via a Log-rank test. At the 21-day experimental end point, the surviving animals (n=8 for TMM001, CLH001, CLH002 groups) were euthanized and the lungs, livers, and spleens were aseptically harvested. The lungs, livers, and spleens were plated for CFU enumeration (n=5) or histopathological evaluation (n=3).

Example 5: Immunocompromised Mouse Survival Study

Anesthetized NSG mice (n=10) were i.n. challenged with either 1.5×10$^4$ CFUs of CSM001 (n=4) or CLH001 (n=6). The mice were monitored for survival for 21 days. Survival curves were generated and analyzed using the Kaplan-Meier method. A significant difference in survival curves was ascertained via a Log-rank test. At the 21-day experimental end point, the surviving animals (n=6 for CLH001) were euthanized and the lungs, livers, and spleens were aseptically harvested. Organs were plated for CFU enumeration (n=4), or histopathological evaluation (n=2).

Example 6: Prime and Boost Vaccination Study

Anesthetized BALB/c mice (n=11) were administered a series of three i.n. vaccinations consisting of 50 1 PBS, 1.5×10$^4$ CFUs or 1.5×10$^5$ CFUs of CLH001 at two week intervals (days −49, −35 and −21 days pre-challenge). At days −35, −21, and −1 pre-challenge, mice (n=3) were anesthetized and retro-orbital blood was collected for antibody analysis. On day 0 prior to challenge, mice (n=3) were euthanized and lungs, livers, and spleens were aseptically removed. Organs from the PBS-vaccinated mice were submitted for histopathological analysis and the organs from the CLH001 vaccinated groups were plated for CFU enumeration. The remaining BALB/c mice (n=8) were i.n. challenged with 1.5×10$^4$ CFU of CSM001. BALB/c mice were monitored for survival for 35 days. Survival curves were generated and analyzed using the Kaplan-Meier method. A significant difference (P≤0.05) was ascertained via a Log-rank test. To determine significant differences in individual treatment as compared to the PBS-treatment control, an additional Log-rank test was employed using an adjusted definition of significance (P≤0.05 of pairwise comparisons). At the 35-day experimental end point, the surviving animals (n=5 for CLH001 [1.5×10$^4$ CFU] and n=8 for CLH001 [1.5×10$^5$ CFU]) were euthanized and the organs were aseptically harvested. Lungs, livers, spleens were plated for CFU enumeration (n=3 for CLH001 [1.5×10$^4$ CFU] and n=5 for CLH001 [1.5×10$^5$ CFU]) and submitted for histopathological evaluation (n=2 for CLH001 [1.5×10$^4$ CFU] and n=3 for CLH001 [1.5×10$^5$ CFU]).

Example 7: High Dose *B. mallei* ATCC 23344 Challenge Prime and Boost Vaccination Study Anesthetized BALB/c mice (n=8 for control group and n=11 for vaccine group) were administered a series of three i.n. vaccinations consisting of 50 μl PBS, or 1.5×10$^5$ CFU of CLH001 at two week intervals (days −49, −35 and −21 days pre-challenge). At days −35, −21, and −1 pre-challenge, mice (n=3) were anesthetized and retro-orbital blood was collected for antibody analysis. On day 0 prior to challenge, mice (n=3 from CLH001-vaccinated group and n=3 for PBS-vaccinated group) were euthanized and their lungs, livers, and spleens were aseptically removed. Organs from the PBS-vaccinated mice were placed in formalin for histopathological analysis while organs from the CLH001 vaccinated groups were plated for CFU enumeration. The remaining BALB/c mice (n=8) were i.n. challenged with 3.5×10$^5$ CFU *B. mallei* ATCC 23344. BALB/c mice were monitored for survival for 35 days. Survival curves were generated and analyzed using the Kaplan-Meier method. A significant difference (P≤0.05) was ascertained via a Log-rank test. Additionally, at 35 days experimental end point, the surviving animals (n=7 from CLH001-vaccinated group) were euthanized and the lungs, livers, and spleens were aseptically harvested and plated for CFU enumeration (n=4). The remaining sets of organs (n=3) were placed in formalin for histopathological evaluation.

Example 8: Organ CFU Enumeration

Histopathological Evaluation

At the indicated time points, anesthetized BALB/c mice were euthanized and lungs, livers and spleens were collected. Organs were placed in 10% formalin, paraffin-embedded, and processed for histopathology. Hematoxylin and eosin stained slides were examined for presence/absence of perivascular and peribronchial infiltrates, necrosis and microabscesses in lungs; granulomas and necrosis in liver; and inflammation and necrosis in spleens, and blindly scored by a pathologist based on the severity using the follow scale: 0 (unremarkable), 1 (minimal), 2 (mild), 3 (moderate) and 4 (severe). Student's t test was performed to ascertain a significant difference in histopathological score between individual treatment as compared to the PBS-treatment control or naïve mice for each organ.

Example 9: *B. mallei*-Specific IgG Total, IgG1, and IgG2a Antibody Analysis

Whole blood was collected via retro-orbital bleeding of anesthetized BALB/c mice. The blood was stored in microvette tubes without anti-coagulant and incubated at room temperature for 20 min to permit clotting. Following centrifugation, serum was collected and stored at −80° C. Samples were inactivated by γ-irradiation using a JL Shepherd Model 109-68 Cobalt-60 Research Irradiator (JL Shepherd & Associates, San Fernando, Calif. 91340). Samples were irradiated on dry ice until 5 MRAD of exposure was reached and sterility was verified by plating 10% of the serum volume on LBG with $FeSO_4$. Irradiated serum from PBS or vaccinated BALB/c mice was evaluated for *B. mallei* specific IgG total, IgG1, IgG2a and IgM using an ELISA performed in 96-well Costar High Binding microplates (Corning, Inc., Corning, N.Y.). Briefly, irradiated *B. mallei* was diluted to a concentration of 10 µg/ml in 1×PBS and wells were coated with 100 µl/well of diluted suspension and incubated overnight at 4° C. Wells were washed twice with wash buffer (1×PBS containing 0.05% Tween-20) and incubated with 250 µl of blocking solution (1×PBS, 1% bovine serum albumin, 0.05% Tween-20) for 2 h at room temperature (RT). After blocking, plates were washed twice with wash buffer. Two-fold dilutions of mouse sera were made with sample diluent (1×PBS, 0.5% bovine serum albumin, and 0.05% Tween-20) in triplicate. One hundred µl of diluted sera along with 100 µl of 1:10,000 anti-Ig class or subclass horseradish peroxidase conjugate (Southern Biotechnology Associates, Inc., Birmingham, Ala.) was added to sample wells and plates were incubated at RT for 2 h. The plates were washed four times with wash buffer prior to addition of 100 µL of Tetramethylbenzidine (TMB) substrate solution (eBioscience, Inc., San Diego, Calif.). After a 15 min, 100 µL of stop solution (2N $H_2SO_4$) was added and the wells were read at 450 nm using an Epoch microplate spectrophotometer (BioTek Instruments, Inc., Winooski, Vt.). The results were reported as the reciprocal of the highest titer giving an optical density (OD) reading of at least 0.1, which was at least twice the background+1 SD. All assays were performed in triplicate, and results were reported as the mean reciprocal endpoint titer+SD.

Example 10: Serum Bactericidal Assay

An overnight culture of *B. mallei* ATCC 23344 was diluted 1:100 in fresh LBG and grown to log phase ($OD_{600}$ of 0.6). The bacterial concentration was adjusted to $1×10^5$ CFU/well in a 96-well plate and incubated with 30% heat inactivated (56° C. for 1 h), pooled CLH001 strain prime and boost vaccinated serum (n=3), or 5 µg/ml anti-*B. mallei* LPS monoclonal antibody (MAb) 3d11 (AbD Serotech, Raleigh, N.C.) in LBG broth containing 22 µl guinea pig complement (Sigma-Aldrich, St. Louis, Mo.). Bacteria incubated in LBG broth containing 30% heat inactivated pooled naïve serum (n=3) and 22 µl guinea pig complement was used as a negative control. After 6 h of incubation (37° C. with 135 rpm), 10-fold serial dilutions were plated on 100 mm LBG agar and incubated for 72 h at 37° C. The bacterial counts were reported as CFU/ml. Each experimental group was assayed in triplicate. A significant difference in bacterial survival between groups was determined using one-way analysis of variance (ANOVA).

CONCLUSIONS

This invention demonstrates the safety and efficacy ion of a *B. mallei* double deletion mutant as a live-attenuated vaccine candidate. Overall, our data indicates that the addition of the Δhcp1 deletion in the TMM001 strain is successful in addressing the persistence issue associated with the TMM001 backbone strain[18]. In all survival and vaccination studies performed (including the NSG mouse study) the vaccine strain was cleared from all target organs by 21 days post-administration. Additionally, histopathology analysis of target organs from animals receiving this vaccine strain showed unremarkable tissue sections. In this study, we have demonstrated that CLH001 is attenuated in vivo. The additional gene deletion in the CLH001 strain provides increased safety and added protection against wild-type reversion and as a result, this has become the first *B. mallei* strain to be excluded from the US Federal Select Agent Program. This exclusion provides an obvious advantage by allowing further vaccine characterization and optimization work to be performed more cost effectively and expeditiously in biosafety level 2 laboratories.

Another advantage of this double mutant is that, unlike the TMM001 backbone strain, its attenuation is not solely dependent on the organism's inability to uptake bound iron sources. Virulence of the TMM001 has been shown to be partially restored when free iron is supplied[18]. Approximately 1% of the Caucasian population suffers from hemochromatosis, an inherited genetic defect resulting in excess free iron. Administration of an iron-deficient strain like TMM001 to this population could potentially result in adverse effects; however, the additional gene deletion of CLH001 eliminates this safety concern. Although not tested for protection against *B. mallei* challenge, mice given 1.5× $10^4$ CLH002 strain (Δhcp1 mutant) showed 100% survival, complete clearance of the lungs and liver, minimal splenic colonization, and minimal liver and spleen histopathology. Taken together, our results indicate that CLH001 may be sufficiently attenuated to be tolerated if inadvertently administered to this population subset.

A number of vaccine studies have examined the correlation between a vaccine's ability to generate high *B. mallei*-specific IgG titers and a Th1-driven immune response (IgG2a:IgG1 ratio ≥1) with its ability to provide protection against *B. mallei* infection[28-32]. Our study supports this assertion, with the greatest protection observed in vaccinated mice (1.5×$10^5$ CFU CLH001) with the highest IgG total titers and IgG2a:IgG1 ratios. This correlation, along with the fact that CLH001-vaccinated serum was able to reduce viable bacterial counts when co-cultured with *B. mallei*, provides evidence that this live attenuated vaccine stimulates a strong humoral response that is at least partially responsible for protection. However, it is widely accepted that the generation of a robust, but appropriate cellular response is also important for protection[14, 15, 17, 33]. Therefore, the Select Agent exclusion status of CLH001 will accelerate experiments to characterize the cellular responses to the vaccine, such as adoptive transfer, T cell recall, and T cell proliferation.

CLH001 represents the first *Burkholderia* vaccine that approaches sterile immunity against high doses of the *B. mallei* CSM001 strain. As such, its inability to provide complete protection and prevent colonization with *B. mallei* ATCC 23344 was unexpected. It is likely that the high challenge dose used was able to overwhelm the immune response generated by CLH001 using our current vaccination regimen. The challenge dose given in this experiment represents a twenty-fold increase over CSM001 bacteria used to challenge in the initial experiment. Although it is evident that further vaccine optimization is required, CLH001 exhibits superior safety and protection as compared to other previously tested vaccines[14-18]. Future optimization will focus on reducing the number of boosts and determining the ideal vaccine dose that will protect against higher dosages of *B. mallei* 23344 and other *B. mallei* strains. This vaccine also has the potential to provide cross-protection against other *Burkholderia* strains, since a pilot study demonstrated that CLH001 was partially protective against a lethal dose of *B. pseudomallei* K96243 (data not shown). The high antibody titers and significant protection achieved in this study provides rationale for vaccine optimization, including increasing the CLH001 vaccine dosage, testing alternative vaccination routes, and/or adding an adjuvant to maximize immune responses. Silva et al., demonstrated that in the closely related organism *B. pseudomallei*, administration of a live attenuated vaccine via subcutaneous route resulted in vigorous recruitment of professional antigen presenting cells (APCs) and stimulated a robust humoral response capable of providing partial protection against lethal i.n. dose challenge with *B. pseudomallei*[34]. Although not clear whether superior to i.n. vaccination in terms of protection, this route of vaccination represents a more conventional and palatable vaccination method that warrants exploration with CLH001. Adjuvants are commonly incorporated into vaccine formulations to increase and/or tailor innate, adaptive and humoral responses. Although our vaccine was not fully protective in the second trial, it is possible that the cellular response elicited by CLH001 was insufficient. Inclusion of the appropriate adjuvant in our vaccination formulation may increase the magnitude of the cellular response generated by CLH001 vaccination alone. One such adjuvant that has shown promise in *B. mallei* and *B. pseudomallei* vaccine formulations and prophylactic therapy is CpG oligodeoxynucleotide (CpG ODN)[35,36]. The CpG ODN is a Toll-like receptor 9 (TLR9) agonist that has been shown to activate B and NK cells, stimulate the antibody production, and drive Th1 cell development[37]. Incorporating an adjuvant like CpG into our vaccine formulation has the potential to increase protection and reduce the number of required vaccine dosages by stimulating a more robust Th1 biased humoral and cellular response. We are confident that continued optimization of this CHL001 strain will result in a live attenuated strain that can be advanced into pre-clinical studies.

Use of Attenuated Bacterial Strains According to the Invention

Attenuated bacteria produced according to the invention will be used to confer prophylactic or therapeutic protection in susceptible hosts against *Burkholderia* infection, e.g., to treat or prevent glanders and melioidosis. The attenuated *Burkholderia* strain may be formulated using known techniques for formulating attenuated bacterial vaccines or immunogenic compositions or bacterial vaccines.

The immunogenic compositions of the present invention may be administered in a number of ways depending upon whether local or systemic treatment is desired. Administration may be topical, pulmonary (e.g., by inhalation or insufflation of powders or aerosols, including by nebulizer; intratracheal, intranasal, epidermal and transdermal), intravesical, oral, or parenteral. Parenteral administration includes intravenous, intraarterial, subcutaneous, intraperitoneal or intramuscular injection or infusion; or intracranial, e.g., intrathecal or intraventricular, administration. Preferably the formulated bacterium containing composition is suitable for intranasal, injection, topical or oral administration, for example as a dried stabilized powder for reconstitution in a suitable buffer prior to administration or in an aerosol composition. In a preferred embodiment the composition is intranasally administered.

Pharmaceutical compositions and formulations for topical administration may include transdermal patches, ointments, lotions, creams, gels, drops, suppositories, sprays, liquids, semisolids, monophasic compositions, multiphasic compositions (e.g., oil-in-water, water-in-oil), foams microsponges, liposomes, nanoemulsions, aerosol foams, polymers, fullerenes, and powders (see, e.g., Taglietti et al. (2008) Skin Ther. Lett. 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvants, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-betacyclodextrin, 2-Phenoxyethanol, Bovine Extract, Polysorbate 80®, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxycholate, Egg Protein, Gentamicin, Hydrocortisone, Octoxynol-10, α-Tocopheryl Hydrogen Succinate, Sodium Deoxycholate, Sodium Phosphate, Beta-Propiolactone, Polyoxyethylene 910, Nonyl Phenol (Triton N-101®, Octoxynol 9), Octoxinol-9 (Triton X-100®), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenol sulfonphthalein), Amphotericin B®, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A®, Mineral oil, Emulsified peanut oil adjuvant (Adjuvant 65®), *Corynebacterium granulosum*-derived P40 component, Lipopolysaccharide, *Mycobacterium* and its components, Cholera toxin, Liposomes, Immunostimulating complexes (ISCOMs), Squalene, and Sodium Chloride.

The vaccine or immunogenic composition may be used in the vaccination of a mammalian host, particularly a human or equine host. A dosage may comprise at least $1.0\times10^2$, $1.0\times10^3$, $1.0\times10^4$, $1.0\times10^5$, or $1.0\times10^6$ CFU's of said live attenuated *Burkholderia* strain or from $10^7$ to $10^{11}$, e.g. from $10^8$ to $10^{10}$, bacteria per dose for a 70 kg adult human host. In some instances the subject may be immunocompromised or may comprise another condition, e.g., another type of infection.

The contents of the following references and all other references which are cited in this application are incorporated by reference in their entirety.

REFERENCES

1 Galyov, E. E., Brett, P. J. & DeShazer, D. Molecular insights into *Burkholderia pseudomallei* and *Burkholderia mallei* pathogenesis. Annu Rev Microbiol 64, 495-517 (2010).

2 Khan, I. et al. Glanders in animals: a review on epidemiology, clinical presentation, diagnosis and countermeasures. Transbound Emerg Dis 60, 204-221 (2013).

3 Van Zandt, K. E., Greer, M. T. & Gelhaus, H. C. Glanders: an overview of infection in humans. Orphanet J Rare Dis 8, 131 (2013).

4 Verma, A. K., Saminathan, M., Tiwari, R., Dahama, K. & Singh, V. Glanders-A re-emerging zoonotic disease: A review. J Bio Sci 14, 38-51 (2014).

5 Howe, C. & Miller, W. R. Human glanders; report of six cases. Annals of internal medicine 26, 93-115 (1947).

6 Srinivasan, A. et al. Glanders in a military research microbiologist. N Engl J Med 345, 256-258 (2001).

7 Malik, P. et al. Emergence and re-emergence of glanders in India: a description of outbreaks from 2006 to 2011. Vet Ital 48, 167-178 (2012).

8 Hornstra, H. et al. Molecular epidemiology of glanders, Pakistan. Emerg Infect Dis 15, 2036-2039 (2009).

9 Scholz, H. C. et al. Genotyping of *Burkholderia mallei* from an outbreak of glanders in Bahrain suggests multiple introduction events. PLoS Negl Trop Dis 8, e3195 (2014).

10 Gregory, C. G. & Waag, D. M. in Medical Aspects of Biological Warfare Textbooks of Military Medicine (ed Z. F. Dembek) Ch. 6, 121-146 (Borden Institute, Walter Reed Army Medical Center, 2007).

11 Currie, B. J. in Principles and Practice of Infectious Diseases (eds G. L. Mandell, J. E. Bennett, & R. Dolin) Ch. 221, 2869-2879 (Churchill Livinston Elsevier, 2010).

12 Wheelis, M. First shots fired in biological warfare. Nature 395, 213 (1998).

13 Alibek, K. & Handelman, S. Biohazard: The Chilling True Story of the Largest Covert Biological Weapons Program in the World. 268-269 (Random House, 1999).

14 Silva, E. B. & Dow, S. W. Development of *Burkholderia mallei* and *pseudomallei* vaccines. Front Cell Infect Microbiol 3, 10 (2013).

15 Mott, T. M., Estes, D. M. & Torres, A. G. in Vaccines Against Bacterial Biothreat Pathogens (eds V. A. Feodorova & V. L. Motin) Ch. Chapter 4, 93-110 (Research Signpost, 2011).

16 Sarkar-Tyson, M. & Titball, R. W. Progress toward development of vaccines against melioidosis: A review. Clin Ther 32, 1437-1445 (2010).

17 Choh, L. C. et al. *Burkholderia* vaccines: are we moving forward? Front Cell Infect Microbiol 3, 5 (2013).

18 Mott, T. M., Vijayakumar, S., Sbrana, E., Endsley, J. J. & Torres, A. G. Characterization of the *Burkholderia mallei* tonB Mutant and Its Potential as a Backbone Strain for Vaccine Development. PLoS Negl Trop Dis 9, e0003863 (2015).

19 Mougous, J. D. et al. A virulence locus of *Pseudomonas aeruginosa* encodes a protein secretion apparatus. Science 312, 1526-1530 (2006).

20 Pukatzki, S. et al. Identification of a conserved bacterial protein secretion system in *Vibrio cholerae* using the Dictyostelium host model system. Proc Natl Acad Sci 103, 1528-1533 (2006).

21 Schell, M. A. et al. Type VI secretion is a major virulence determinant in *Burkholderia mallei*. Mol Microbiol 64, 1466-1485 (2007).

22 Burtnick, M. N., DeShazer, D., Nair, V., Gherardini, F. C. & Brett, P. J. *Burkholderia mallei* cluster 1 type VI secretion mutants exhibit growth and actin polymerization defects in RAW 264.7 murine macrophages. Infect Immun 78, 88-99 (2010).

23 Burtnick, M. N. et al. The cluster 1 type VI secretion system is a major virulence determinant in *Burkholderia pseudomallei*. Infect Immun 79, 1512-1525 (2011).

24 Duval, C. W. & White, P. G. The Histological Lesions of Experimental Glanders. J Exp Med 9, 352-380 (1907).

25 Harley, V. S., Dance, D. A., Drasar, B. S. & Tovey, G. Effects of *Burkholderia pseudomallei* and other *Burkholderia* species on eukaryotic cells in tissue culture. Microbios 96, 71-93 (1998).

26 Kespichayawattana, W., Rattanachetkul, S., Wanun, T., Utaisincharoen, P. & Sirisinha, S. *Burkholderia pseudomallei* induces cell fusion and actin-associated membrane protrusion: a possible mechanism for cell-to-cell spreading. Infect Immun 68, 5377-5384 (2000).

27 Massey, S. et al. In vivo Bioluminescence Imaging of *Burkholderia mallei* Respiratory Infection and Treatment in the Mouse Model. Front Microbiol 2, 174 (2011).

28 Amemiya, K., Bush, G. V., DeShazer, D. & Waag, D. M. Nonviable *Burkholderia mallei* induces a mixed Th1- and Th2-like cytokine response in BALB/c mice. Infect Immun 70, 2319-2325 (2002).

29 Amemiya, K. et al. Interleukin-12 induces a Th1-like response to *Burkholderia mallei* and limited protection in BALB/c mice. Vaccine 24, 1413-1420 (2006).

30 Bandara, A. B. et al. A disruption of ctpA encoding carboxy-terminal protease attenuates *Burkholderia mallei* and induces partial protection in CD1 mice. Microb Pathog 45, 207-216 (2008).

31 Ulrich, R. L., Amemiya, K., Waag, D. M., Roy, C. J. & DeShazer, D. Aerogenic vaccination with a *Burkholderia mallei* auxotroph protects against aerosol-initiated glanders in mice. Vaccine 23, 1986-1992 (2005).

32 Nieves, W. et al. A naturally derived outer-membrane vesicle vaccine protects against lethal pulmonary *Burkholderia pseudomallei* infection. Vaccine 29, 8381-8389 (2011).

33 Bondi, S. K. & Goldberg, J. B. Strategies toward vaccines against *Burkholderia mallei* and *Burkholderia pseudomallei*. Expert Rev Vaccines 7, 1357-1365 (2008).

34 Silva, E. B. et al. Correlates of immune protection following cutaneous immunization with an attenuated *Burkholderia pseudomallei* vaccine. Infect Immun 81, 4626-4634 (2013).

35 Whitlock, G. C. et al. Protective response to subunit vaccination against intranasal and challenge. Procedia Vaccinol 2 (2010).

36 Judy, B. M. et al. Prophylactic application of CpG oligonucleotides augments the early host response and confers protection in acute melioidosis. PLoS One 7, e34176 (2012).

37 Vollmer, J. et al. Characterization of three CpG oligodeoxynucleotide classes with distinct immunostimulatory activities. Eur J Immunol 34, 251-262 (2004).

One skilled in the art will readily appreciate that the present invention is adapted to carry out the objects and obtain the ends and advantages mentioned, as well as those inherent therein. The prior examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

What is claimed is:

1. A live attenuated *Burkholderia* strain containing mutations which result in the disruption in the expression or functionality of the gene products encoded by the tonB gene and the hcp1 gene, wherein the *Burkholderia* strain is *Burkholderia mallei* strain or *Burkholderia pseudomallei* strain.

2. The live attenuated *Burkholderia* strain of claim 1, which is the *Burkholderia mallei* strain.

3. The live attenuated *Burkholderia mallei* strain of claim 2, wherein said strain comprises mutations which reduce or eliminate the expression of the tonB gene and the hcp1 gene.

4. The live attenuated *Burkholderia mallei* strain of claim 2, wherein the expression of the tonB gene and the hcp1 gene in the attenuated *Burkholderia mallei* strain is eliminated by the deletion of the promoters regulating the expression of the tonB gene and the hcp1 gene.

5. The live attenuated *Burkholderia mallei* strain of claim 2, wherein said strain elicits immunoprotection against *Burkholderia mallei* in a mammalian host, (ii) does not persist in vivo, and (iii) does not revert to the wild-type strain after administration to a susceptible host.

6. The live attenuated *Burkholderia mallei* strain of claim 2, wherein the strain is *B. mallei* ΔtonB Δhcp1 CLH001 strain which has been deposited at The Biodefense and Emerging Infections Research Resources Repository (BEI Repository).

7. The live attenuated *Burkholderia mallei* strain of claim 6, wherein the strain comprises the 162 base pair intragenic in-frame deletion in the hcp1 gene.

8. An immunogenic composition comprising the live attenuated *Burkholderia* strain according to claim 1, which further comprises at least one pharmaceutically acceptable carrier or excipient.

9. An immunogenic composition comprising the live attenuated *Burkholderia mallei* strain according to claim 2, which further comprises at least one pharmaceutically acceptable carrier or excipient.

10. The immunogenic composition of claim 8, which is suitable for subcutaneous, inhalatory or intranasal administration.

11. The immunogenic composition of claim 10, wherein the composition is aerosolized.

12. The immunogenic composition of claim 8, which further comprises an immune adjuvant.

13. The immunogenic composition of claim 12, wherein the immune adjuvant is selected from a TLR agonist, a CD40 agonist, saponin, and ALUM (aluminum hydroxide).

14. The immunogenic composition of claim 13, wherein the TLR agonist is a TLR9 agonist.

* * * * *